(12) United States Patent
Cai et al.

(10) Patent No.: US 7,476,741 B2
(45) Date of Patent: Jan. 13, 2009

(54) SUBSTITUTED 4H-CHROMENS, 2H-CHROMENES, CHROMANS AND ANALOGS AS ACTIVATORS OF CASPASES AND INDUCERS OF APOPTOSIS AND THE USE THEREOF

(75) Inventors: Sui Xiong Cai, San Diego, CA (US); Songchun Jiang, San Diego, CA (US); Giorgio Attardo, Laval (CA); Réal Denis, Montreal (CA); Richard Storer, Pinner (GB); Rabindra Rej, Montreal (CA)

(73) Assignees: Cytovia, Inc., San Diego, CA (US); Shire BioChem, Inc., Quebec (CA)

( * ) Notice: Subject to any disclaimer, the term of this patent is extended or adjusted under 35 U.S.C. 154(b) by 421 days.

(21) Appl. No.: 10/514,426

(22) PCT Filed: May 16, 2003

(86) PCT No.: PCT/US03/15432

§ 371 (c)(1),
(2), (4) Date: Nov. 16, 2004

(87) PCT Pub. No.: WO03/096982

PCT Pub. Date: Nov. 27, 2003

(65) Prior Publication Data

US 2005/0176750 A1    Aug. 11, 2005

Related U.S. Application Data

(60) Provisional application No. 60/378,043, filed on May 16, 2002, now abandoned.

(51) Int. Cl.
C07D 405/00 (2006.01)
(52) U.S. Cl. ............ 546/282.7; 546/283.1; 549/385; 549/399; 549/405; 548/430; 548/577
(58) Field of Classification Search .......... 549/385, 549/399, 404; 548/430, 577; 546/282.7, 546/283.1
See application file for complete search history.

(56) References Cited

U.S. PATENT DOCUMENTS

| | | |
|---|---|---|
| 4,303,656 A | 12/1981 | Sime et al. |
| 4,698,345 A | 10/1987 | Dicker et al. |
| 5,281,619 A | 1/1994 | Dell et al. |
| 5,284,868 A | 2/1994 | Dell et al. |
| 5,434,160 A | 7/1995 | Dell et al. |
| 5,514,706 A | 5/1996 | Ambler et al. |
| 5,571,818 A | 11/1996 | Williams |
| 5,574,034 A | 11/1996 | Williams |
| 5,576,325 A | 11/1996 | Williams |
| 5,624,953 A | 4/1997 | Ambler et al. |
| 5,637,589 A | 6/1997 | Lee et al. |
| 5,726,204 A | 3/1998 | Lee et al. |
| 5,741,818 A | 4/1998 | Dimmock |
| 5,847,165 A | 12/1998 | Lee et al. |
| 5,902,792 A | 5/1999 | Jayaram |
| 5,994,390 A | 11/1999 | Jacobsen et al. |
| 6,160,010 A | 12/2000 | Uckun et al. |
| 6,221,900 B1 | 4/2001 | Uckun et al. |
| 6,258,824 B1 | 7/2001 | Yang |
| 6,294,575 B1 | 9/2001 | Uckun et al. |
| 6,303,652 B1 | 10/2001 | Uckun et al. |
| 6,323,228 B1 | 11/2001 | BaMaung et al. |
| 6,365,626 B1 | 4/2002 | Uckun et al. |
| 6,388,092 B2 | 5/2002 | Yang |
| 6,828,091 B2 | 12/2004 | Kasibhatla et al. |
| 6,858,607 B1 | 2/2005 | Cai et al. |
| 6,858,609 B2 | 2/2005 | Janssen et al. |
| 6,906,203 B1 | 6/2005 | Drewe et al. |
| 7,015,328 B2 | 3/2006 | Cai et al. |
| 7,053,117 B2 | 5/2006 | Cai et al. |
| 7,135,480 B2 | 11/2006 | Cai et al. |
| 7,235,674 B2 | 6/2007 | Cai et al. |
| 2003/0065018 A1 | 4/2003 | Cai et al. |
| 2003/0114485 A1 | 6/2003 | Cai et al. |
| 2005/0090526 A1 | 4/2005 | Cai et al. |
| 2005/0154015 A1 | 7/2005 | Drewe et al. |
| 2005/0165053 A1 | 7/2005 | Cai et al. |
| 2006/0035925 A1 | 2/2006 | Cai et al. |
| 2006/0104998 A1 | 5/2006 | Cai et al. |
| 2007/0253957 A1 | 11/2007 | Zhang et al. |

FOREIGN PATENT DOCUMENTS

| | | |
|---|---|---|
| EP | 0 481 243 A1 | 4/1992 |
| EP | 0 537 949 A1 | 4/1993 |
| EP | 0 599 514 A2 | 6/1994 |
| EP | 0 619 314 A1 | 10/1994 |
| EP | 0 618 206 B1 | 9/1997 |

(Continued)

OTHER PUBLICATIONS

McGraw—Hill Dictionary of Chemical Terms(1990) pp. 282.*
Concise Encyclopedia Chemistry (1993), pp. 490.*
Hawley's Condensed Chemical Dictionary (1993), pp. 594.*

(Continued)

*Primary Examiner*—Janet L. Andres
*Assistant Examiner*—Raymond Covington
(74) *Attorney, Agent, or Firm*—Sterne, Kessler, Goldstein & Fox P.L.L.C.

(57) ABSTRACT

The present invention is directed to substituted 4H-chromenes, 2H-chromenes, chromans and analogs thereof, represented by the general Formula (I) wherein $R_5$, A, B, X, Y, Z and dotted lines are defined herein. The present invention also relates to the discovery that compounds having Formula (I) are activators of caspases and inducers of apoptosis. Therefore, the activators of caspases and inducers of apoptosis of this invention can be used to induce cell death in a variety of clinical conditions in which uncontrolled growth and spread of abnormal cells occurs.

23 Claims, No Drawings

FOREIGN PATENT DOCUMENTS

| WO | WO 96/20721 A1 | 7/1996 |
| --- | --- | --- |
| WO | WO 98/24427 A2 | 6/1998 |
| WO | WO 99/18856 A1 | 4/1999 |
| WO | WO 99/54286 A2 | 10/1999 |
| WO | WO 99/62510 A2 | 12/1999 |
| WO | WO 00/04901 | 2/2000 |
| WO | WO 00/47574 A1 | 8/2000 |
| WO | WO 01/34591 A2 | 5/2001 |
| WO | WO 02/092076 A1 | 11/2002 |
| WO | WO 02/092083 A1 | 11/2002 |
| WO | WO 02/092594 A1 | 11/2002 |
| WO | WO 03/096982 A2 | 11/2003 |
| WO | WO 03/097806 A3 | 11/2003 |

OTHER PUBLICATIONS

Abstract of Elgamal, M.H.A., et al., "Synthesis of some novel nitrogenous furocoumarin derivatives," *Polish J. Chem.* 72:735-745, Polish Chemical Society (1998), Accession No. 128:321530 CA.

Abstract of El-Taweel, M.A.E.A., et al., "Synthesis of 4H-naphtho[2,1-b]pyrans, benzo [h] coumarins, 4H-naphtho[2,1-b:6.5-b]dipyrans 4H-naphtho[1,2-b:3,4-b'] dipyrans and pyridine derivatives," *Anales de Quimica* 91:589-593, Real Sociedad Espanola de Quimica (1995), Accession No. 125:114568 CA.

Abstract of European Patent No. EP 0 481 243, Meguro, K. et al., "Tricyclic heterocyclic compounds, their production and use," Accession No. 117:69733 CA.

Abstract of Radwan, A.M., et al., "A new route for the synthesis of 1,2,4-triazole and 3,4-disubstituted cinnoline derivatives," *J. Chem. Soc. Pakistan* 17:113-117, Chemical Society of Pakistan (1995), Accession No. 124:117193 CA.

Abstract of Tawada, H., al., "Synthesis of 3-ureido derivatives of coumarin and 2-quinolone as potent acyl-CoA: cholesterol acyltransferase inhibitors," *Chem. Pharm. Bull.* 43:616-625, Pharmaceutical Society of Japan (1995), Accession No. 123:339669 CA.

Abstract of Woods, L.L. and Sterling, J., "New synthesis of naphtho[1,2-b]pyran-2-ones," *J. Org. Chem.* 29:502-504, American Chemical Society (1964), Accession No. 60:44584 CA.

Abstract of Al-Mousawa, S.M., et al., "Synthesis of New Condensed 2-Amino-4H-pyran-3-carbonitriles and of 2-Aminoquinoline-3-carbonitriles," *Organic Preparations and Procedures Int.* 31:305-313, Organic Preparations and Procedures, Inc. (1999), CAPLUS Accession No. 131:199593, 2 pages (1999).

Al-Mousawi, S.M., et al., "Synthesis of New Condensed 2-Amino-4H-pyran-3-carbonitriles and of 2-Aminoquinoline-3-carbonitriles," *Organic Preparations and Procedures Int.* 31:305-313, Organic Preparations and Procedures, Inc. (1999).

*Apoptosis and Cancer Chemotherapy*, Hickman, J.A. and Dive, C., eds., Humana Press, Totowa, NJ (1999), 4 pages (includes Title Page, Foreword, Preface, Contents and Contributors).

Batteux, F., et al., "Gene Therapy of Experimental Autoimmune Thyroiditis by In Vivo Administration of Plasmid DNA Coding for Fas Ligand," *J. Immunol.* 162: 603-608, The American Association of Immunologists (1999).

Birch, K.A., et al., "LY290181, an Inhibitor of Diabetes-Induced Vascular Dysfunction, Blocks Protein Kinase C-Stimulated Transcriptional Activation Through Inhibition of Transcription Factor Binding to a Phorbol Response Element," *Diabetes* 45:642-650, The American Diabetes Association (1996).

Bloxham, J., et al., "Preparation of Some New Benzylidenemalononitriles by an $S_NAr$ Reaction: Application to Naphtho[1,2-b]pyran Synthesis," *Heterocycles* 38:399-408, The Japanese Institute of Heterocyclic Chemistry (1994).

Boirivant, M.; et al., "Lamina Propria T Cells in Crohn's Disease and Other Gastrointestinal Inflammation Show Defective CD2 Pathway-Induced Apoptosis," *Gastroenterol.* 116:557-565, Elsevier, Inc. (1999).

Bremner, A.R.F. and Beattie, R.M., "Therapy of Crohn's disease in childhood," *Expert Opin. Pharmacother.* 3:809-825, Ashley Publications Ltd. (2002).

Chandrasekhar, S., et al., "Identification of a Novel Chemical Series That Blocks Interleukin-1-Stimulated Metalloprotease Activity in Chondrocytes," *J. Pharmacol. Exper. Ther.* 273:1519-1528, The American Society for Pharmacology and Experimental Therapeutics (1995).

Coven, T.R., et al., "PUVA-induced lymphocyte apoptosis: Mechanism of action in psoriasis," *Photoderm. Photoimmunol. Photomed.* 15:22-27, Munksgaard (1999).

Elagamey, A.G.A., et al., "Nitriles In Heterocyclic Synthesis: Novel Syntheses of Benzo[b]pyrans, Naphtho[1,2-b]pyrans, Naphtho[2,1-b]pyrans, Pyrano[3,2-h]quinolines and Pyrano[3,2-c]quinolines," *Collection Czechoslovak Chem. Commun.* 53:1534-1538, Czechoslovak Academy of Sciences (1988).

Elagamey, A.G.A. and El-Taweel, F.M.A.A., "Nitriles in heterocyclic synthesis: Synthesis of condensed pyrans," *Indian J. Chem.* 29B:885-886, The Council of Scientific & Industrial Research, New Delhi (1990).

Elgert, K.D., "Immunology—Understanding the Immune System," pp. 315-331, John Wiley & Sons, Inc. (1996).

Ellis, R.E., et al., "Mechanisms and Functions of Cell Death," *Ann. Rev. Cell Biol.* 7:663-698, Annual Reviews, Inc. (1991).

Friesen, C., et al., "Involvement of the CD95 (APO-1/Fas) receptor/ligand system in drug-induced apoptosis in leukemia cells," *Nat. Med.* 2:574-577, Nature Publishing Co. (1996).

Gourdeau, H., et al., "Antivascular and antitumor evaluation of 2-amino-4-(3-bromo-4,5-dimethoxy-phenyl)-3-cyano-4-*H*-chromenes, a novel series of anticancer agents," *Mol. Cancer Ther.* 3:1375-1383, American Association for Cancer Research (Nov. 2004).

Greenwald, R.B., et al., "Drug Delivery Systems Employing 1,4- or 1,6-Elimination: Poly(ethylene glycol) Prodrugs of Amine-Containing Compounds," *J. Med. Chem.* 42:3657-3667, American Chemical Society (1999).

Heenen, M., et al., "Methotrexate induces apoptotic cell death in human keratinocytes," *Arch. Dermatol. Res.* 290:240-245, Springer-Verlag (1998).

Infante, A.J., et al., "The clinical spectrum in a large kindred with autoimmune lymphoproliferative syndrome caused by a Fas mutation that impairs lymphocyte apoptosis," *J. Pediatr.* 133:629-633, Mosby, Inc. (1998).

Kasibhatla, S., et al., "Discovery and mechanism of action of a novel series of apoptosis inducers with potential vascular targeting activity," *Mol. Cancer Ther.* 3:1365-1373, American Association for Cancer Research (Nov. 2004).

Kemnitzer, W., et al., "Discovery of 4-Aryl-4*H*-chromenes as a New Series of Apoptosis Inducers Using a Cell- and Caspase-based High-Throughput Screening Assay. 1. Structure-Activity Relationships of the 4-Aryl Group," *J. Med. Chem.* 47: 6299-6310, American Chemical Society (Dec. 2004).

Kemnitzer, W. et al., "Discovery of 4-aryl-4*H*-chromenes as a new series of apoptosis inducers using a cell- and caspase-based high-throughput screening assay. 2. Structure-activity relationships of the 7- and 5-, 6-, 8-positions," *Bioorg. Med. Chem. Letts.* 15:4745-4751, Elsevier Ltd. (Nov. 2005).

Klokol, G.V., et al., "Cyclization of Nitriles. XXIII. Addition of Active Phenols to Electron-Deficient Ethylenes, Accompanied by Cyclization to 2-Amino-4H-benzo[b]pyrans. Crystal Structure of 2-Amino-4-(2-fluorophenyl)-3-ethoxycarbonyl-4H-naphtho[2,1-b]pyran," *J. Organic Chem. of USSR* 23:369-377, Plenum Publishing Corporation (1987).

Klokol, G.V., et al., "Cyclization of nitriles. XXIII. Addition of active phenols to electron-deficient ethylenes with cyclization to 2-amino-4H-benzo[b]pyrans. Crystal structure of 2-amino-4-(2-fluorophenyl)-3-(ethoxycarbonyl)4H-naphtho[2,1-b]pyran," *Chem. Abstr.* 108:5822c, Chemical Abstracts Service (1988).

Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem.* 42: 3623-3628, American Chemical Society (1999).

López-Hoyos, M., et al., "Regulation of B cell apoptosis by Bcl-2 and Bcl-$X_L$ and its role in the development of autoimmune diseases (Review)," *Intl. J. Mol. Med.* 1:475-483, D.A. Spandidos (1998).

Los, M., et al., "Cross-Resistance of CD95- and Drug-Induced Apoptosis as a Consequence of Deficient Activation of Caspases (ICE/Ced-3 Proteases)," *Blood* 90: 3118-3129, W.B. Saunders Company (1997).

Ohsako, S. and Elkon, K.B., "Apoptosis in the effector phase of autoimmune diabetes, multiple schlerosis and thyroiditis," *Cell Death Diff.* 6:13-21, Stockton Press (1999).

O'Reilly, L.A. and Strasser, A., "Apoptosis and autoimmune disease," *Inflamm. Res.* 48:5-21, Birkhäuser Verlag, Basel (1999).

Orrenius, S., "Apoptosis: molecular mechanisms and implications for human disease," *J. Internal Med.* 237:529-536, Blackwell Science Ltd. (1995).

Ozawa, M., et al., "312-nanometer Ultraviolet B Light (Narrow-Band UVB) Induces Apoptosis of T Cells within Psoriatic Lesions," *J. Exp. Med.* 189:711-718, The Rockefeller University Press (1999).

Panda, D., et al., "Suppression of Microtubule Dynamics by LY290181," *J. Biol. Chem.* 272:7681-7687, The American Society for Biochemistry and Molecular Biology, Inc. (1997).

Paull, K.D., et al., "Identification of Novel Antimitotic Agents Acting at the Tubulin Level by Computer-assisted Evaluation of Differential Cytotoxicity Data," *Can. Res.* 52:3892-3900, The American Association for Cancer Research, Inc. (1992).

Radwan, S.M., et al., "Synthesis and Some Reactions of New Benzo[*b*]pyran Derivatives," *Phosphorus, Sulfur, and Silicon* 101:207-211, Overseas Publishers Association (1995).

Ram, V.J. and Verma, M., "Synthesis of 4*H*-benzopyrans, benzopyrano[2,3-*d*]pyrimidines and related compounds as biodynamic agents," *Ind. J. Chem.* 33B:908-911, Publications & Information Directorate (CSIR) (1994).

Robinson, M., "Medical Therapy of Inflammatory Bowel Disease for the 21$^{st}$ Century," *Eur. J. Surg.* 164(*Suppl. 582*):90-98, Scandinavian University Press (1998).

Savill, J., "Apoptosis in resolution of inflammation," *J. Leukoc. Biol.* 61:375-380, Society for Leukocyte Biology (1997).

Schmitt, E., et al., "The Bcl-xL and Bax-α control points: modulation of apoptosis induced by cancer chemotherapy and relation to TPCK-sensitive protease and caspase activation," *Biochem. Cell Biol.* 75:301-314, National Research Council of Canada (1997).

Sen, S. and D'Incalci, M., "Apoptosis: Biochemical events and relevance to cancer chemotherapy," *FEBS* 307:122-127, Elsevier Science Publishers B.V. (1992).

Sharanin, Y.A. and Klokol, G.V., "Synthesis of 2-amino-4H-chromenes," *Chem. Abstr.* 99:212393z, Chemical Abstracts Service (1983).

Sharanin, Y.A. and Klokol, G.V., "Synthesis of 2-Amino-4H-chromenes," *J. Organic Chem. of USSR* 19:1582-1583, Plenum Publishing Corporation (1984).

Shevach, E.M., "Animal Models for Autoimmune and Inflammatory Disease," *Current Protocols in Immunology, Suppl.* 52:15.0.1-15.0.6, John Wiley & Sons, Inc. (2002).

Simone, J.V., "Oncology: Introduction," *Cecil Textbook of Medicine*, 20$^{th}$ Edition, Bennett, J.C. and Plum, F., eds., vol. 1, pp. 1004-1010, W.B. Saunders Company (1996).

Singh, B., et al., "Immune therapy in inflammatory bowel disease and models of colitis," *Brit. J. Surg.* 88:1558-1569, Blackwell Science Ltd. (2001).

Smith, C.W., et al., "The Anti-Rheumatic Potential of a Series of 2,4-Di-substituted-4H-naphtho[1,2-b]pyran-3-carbonitriles," *Biorg. Med. Chem. Lett.* 5:2783-2788, Elsevier Science Ltd. (1995).

Supplementary Partial European Search Report for European Patent Application No. 02741704.7, European Patent Office, The Hague, Netherlands, 6 pages, dated Aug. 30, 2005.

Thornberry, N.A., et al., "A Combinatorial Approach Defines Specificities of Members of the Caspase Family and Granzyme B," *J. Biol. Chem.* 272:17907-17911, The American Society for Biochemistry and Molecular Biology, Inc. (1997).

Thornberry, N.A., "Caspases: key mediators of apoptosis," *Chem. Biol.* 5:R97-R103, Current Biology Ltd. (1998).

Thornberry, N.A., "The caspase family of cysteine proteases," *Brit. Med. Bull.* 53:478-490, Oxford University Press (1997).

Vaishnaw, A.K., et al., "The molecular basis for apoptotic defects in patients with CD95 (Fas/Apo-1) mutations," *J. Clin. Invest.* 103:355-363, American Society for Clinical Investigation (1999).

Wachlin, G., et al., "IL-1β, IFNγ and TNF-α increase vulnerability of pancreatic beta cells to autoimmune destruction," *J. Autoimmunity* 20:303-312, Elsevier Science Ltd. (Jun. 2003).

Wakisaka, S., et al., "Modulation of proinflammatory cytokines of Fas/Fas ligand-mediated apoptotic cell death of synovial cells in patients with rheumatoid arthritis (RA)," *Clin. Exp. Immunol.* 114:119-128, Blackwell Science (1998).

Wiernicki, T.R., et al., "Inhibition of Vascular Smooth Muscle Cell Proliferation and Arterial Intimal Thickening by a Novel Antiproliferative Naphthopyran," *J. Pharmacol. Exper. Ther.* 278:1452-1459, The American Society for Pharmacology and Experimental Therapeutics (1996).

Wood, D.L., et al., "Inhibition of Mitosis and Microtubule Function through Direct Tubulin Binding by a Novel Antiproliferative Naphthopyran LY290181," *Mol. Pharmacol.* 52:437-444, Williams & Wilkins (1997).

Wyllie, A.H., "Cell death: a new classification separating apoptosis from necrosis," in *Cell death in biology and pathology*, Bowen, I.D. and Lockshin, R.A., eds., Chapman and Hall, London, pp. 9-34 (1981).

Wyllie, A.H., et al., "Cell Death: The Significance of Apoptosis," *Int. Rev. Cyt.* 68251-306, Academic Press, Inc. (1980).

Zhou, T., et al., "Bisindolylmaleimide VIII facilitates Fas-mediated apoptosis and inhibits T cell-mediated autoimmune diseases," *Nature Med.* 5:42-48, Nature Publishing Group (1999).

*Zhurnal organicheskoi khimii* 19:1782-1784, Moscow Izdatelstvo Nauka (1983).

International Search Report for International Application No. PCT/US03/15432, United States Patent Office, Alexandria, Virginia, mailed on Jun. 4, 2004.

Prosecution history for Cai, S.X. et al., U.S. Appl. No. 10/146,139, filed May 16, 2002, now patented as 6,858,607 B1.

Prosecution history for Drewe, J.A. et al., U.S. Appl. No. 09/705,840, filed Nov. 6, 2000, now patented as 6,906,203 B1.

Office Action for U.S. Appl. No. 10/989,057, Cai, S.X., et al., filed Nov. 16, 2004, mailed Mar. 16, 2006.

Copending U.S. Appl. No. 10/514,427, inventors: Cai, S.X, et al., filed Nov. 16, 2004 (not published).

Murray, Jeffrey H., Office Action for U.S. Appl. No. 11/150,586, U.S. Patent and Trademark Office, Alexandria, Virginia, mailed Nov. 27, 2007.

O'Dell, David K. Office Action for U.S. Appl. No. 10/514,427, U.S. Patent and Trademark Office, Alexandria, Virginia mailed Nov. 9, 2007.

Co-pending Application No. 11/822,535, inventors Cai, S.X. et al., filed Jul. 6, 2007 (not published).

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal acetyl
<220> FEATURE:
<221> NAME/KEY: MOD_RES
<222> LOCATION: (4)..(4)
<223> OTHER INFORMATION: C-terminal N'-ethoxycarbonyl-Rhodamine 110

<400> SEQUENCE: 1

Asp Glu Val Asp
1

SUBSTITUTED 4H-CHROMENS, 2H-CHROMENES, CHROMANS AND ANALOGS AS ACTIVATORS OF CASPASES AND INDUCERS OF APOPTOSIS AND THE USE THEREOF

BACKGROUND OF THE INVENTION

1. Field of the Invention

This invention is in the field of medicinal chemistry. In particular, the invention relates to substituted 4H-chromenes, 2H-chromenes, chromans and analogs, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death, or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal—they become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, e.g., colon cancers, exist primarily in the $G_o$ phase, whereas rapidly proliferating normal tissues, e.g., bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP537949 discloses derivatives of 4H-naphtho[1,2-b]pyran as antiproliferatives:

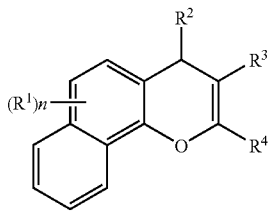

wherein, each $R^1$ is independently halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —COOR$^5$ where $R^5$ is an ester group, —CONR$^6$R$^7$ or —NR$^6$R$^7$ where $R^6$ and $R^7$ are each hydrogen or $C_{1-4}$ alkyl;

$R^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or $R^2$ is furanyl optionally substituted with $C_{1-4}$ alkyl;

$R^3$ is nitrile, carboxy, —COOR$^8$ where $R^8$ is an ester group, —CONR$^9$R$^{10}$ where $R^9$ and $R^{10}$ are each hydrogen or $C_{1-4}$ alkyl or $R^{11}$SO$_2$ where $R^{11}$ is $C_{1-4}$ alkyl or optionally substituted phenyl;

$R^4$ is —NR$^{12}$R$^{13}$, —NHCOR$^{12}$, —N(COR$^{12}$)$_2$ or —N=CHOCH$_2$R$^{12}$ where $R^{12}$ and $R^{13}$ are each hydrogen or $C_{1-4}$ alkyl optionally substituted with carboxy,

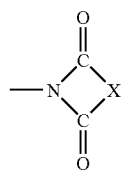

where X is $C_{2-4}$ alkylene, or $R^4$ is —NHSO$_2$R$^{14}$ where $R^{14}$ is $C_{1-4}$ alkyl or optionally substiuted phenyl; and n is 0-2.

U.S. Pat. No. 5,281,619 discloses naphthopyrans for therapy of diabetic complications:

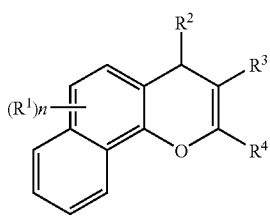

wherein, $R^1$ is $C_{1-4}$ alkoxy, OH or COOH;

$R^2$ is optionally substituted phenyl;

$R^3$ is nitrile, or $R^3$ is carboxy or —COOR$^8$ when $R^2$ is phenyl substituted with 3-nitro or 3-trifluoromethyl and $R^8$ is an ester group;

$R^4$ is NR$^{12}$R$^{13}$, —NHCOR$^{12}$, —N(COR$^{12}$)$_2$ or —N=CHOCH$_2$R$^{12}$, wherein $R^{12}$ and $R^{13}$ are each H or $C_{1-4}$ alkyl; and n is 0-2.

EP599514 discloses the preparation of pyranoquinoline derivatives as inhibitors of cell proliferation:

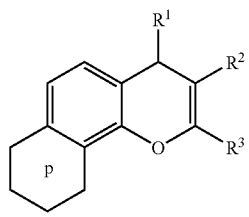

wherein $R^1$ is optionally substituted phenyl or optionally substituted heteroaryl selected from thienyl, pyridyl, benzothienyl, quinolinyl, benzofuranyl or benzimidazolyl, or $R^1$ is furanyl optionally substituted with $C_{1-4}$ alkyl;

$R^2$ is nitrile, carboxy, —CO$_2$R$^4$ wherein $R^4$ is an ester group, —CON(R$^5$)R$^6$ where $R^5$ and $R^6$ are independently H or $C_{1-4}$ alkyl, or R$^7$SO$_2$ where $R^7$ is $C_{1-4}$ alkyl or optionally substituted phenyl;

$R^3$ is —NR$^8$R$^9$, —NHCOR$^8$, —N(CO$_2$R$^8$)$_2$, —N=CHOR$^8$ where $R^8$ and $R^9$ are independently H or $C_{1-4}$ alkyl, or —NHSO$_2$R$^{10}$ where $R^{10}$ is $C_{1-4}$ alkyl or optionally substituted phenyl, or

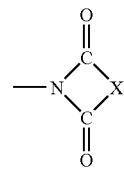

where X is $C_{2-4}$ alkylene; and the ring P represents a pyridine fused to the benzopyran nucleus.

EP618206 discloses the preparation of naphthopyran and pyranoquinoline as immunosuppressants and cell proliferation inhibitors:

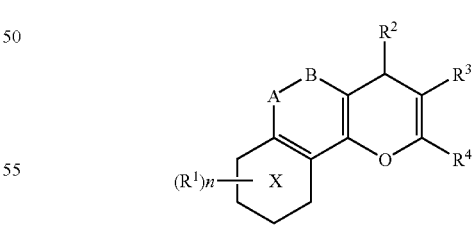

wherein,

A-B is CH$_2$CH$_2$ or CH=CH;

each $R^1$ is independently halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$alkoxy, nitrogen-containing heterocyclyl, nitro, trifluoromethoxy, —COOR$^5$ where $R^5$ is an ester group, —COR$^6$, —CONR$^6$R$^7$ or —NR$^6$R$^7$ where $R^6$ and $R^7$ are each hydrogen or $C_{1-4}$ alkyl;

R² is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or R² is furanyl optionally substituted with $C_{1-4}$ alkyl;

R³ is nitrile, carboxy, —COOR⁸ where R⁸ is an ester group, —CONR⁹R¹⁰ where R⁹ and R¹⁰ are each hydrogen or $C_{1-4}$ alkyl, or —SO₂R¹¹ where R¹¹ is $C_{1-4}$ alkyl or optionally substituted phenyl-$C_{1-4}$ alkyl;

R⁴ is 1-pyrrolyl, 1-imidazolyl or 1-pyrazolyl, each of which is optionally substituted by one or two $C_{1-4}$ alkyl, carboxyl, hydroxyl-$C_{1-4}$alkyl or —CHO groups, or R⁴ is 1-(1,2,4-triazolyl), 1-(1,3,4-triazolyl) or 2-(1,2,3-triazolyl), each of which is optionally substiuted by a $C_{1-4}$ alkyl or $C_{1-4}$ perfluoroalkyl group, or R⁴ is 1-tetrazolyl optionally substituted by $C_{1-4}$ alkyl;

X is a pyridine or a benzene ring; and n is 0-2.

EP619314 discloses the preparation of 4-phenyl-4H-naphtho(2,1-b)pyran derivatives:

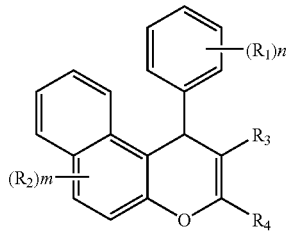

wherein,

R₁ and R₂ are independently halo, trifluoromethyl, $C_1$-$C_4$ alkoxy, hydroxy, nitro, $C_1$-$C_4$ alkyl, $C_1$-$C_4$ alkylthio, hydroxy-$C_1$-$C_4$ alkyl, hydroxy-$C_1$-$C_4$ alkoxy, trifluoromethoxy, carboxy, —COOR₈ where R₈ is an ester group, —COR₉, —CONR₉R₁₀ or —NR₉R₁₀ where R₉ and R₁₀ are each hydrogen or $C_1$-$C_4$ alkyl;

R₃ is nitrile, carboxy or —CO₂R₁₁ wherein R₁₁ is an ester group;

R₄ is —NR₁₂R₁₃, —NR₁₂COR₁₃, —N(COR₁₂)₂ or —N=CHOCH₂R₁₂ where R₁₂ and R₁₃ are each hydrogen or $C_{1-4}$ alkyl, or R₄ is

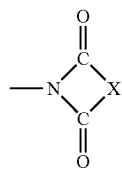

where X is $C_2$-$C_4$ alkylene, or R₄ is optionally substituted 1-pyrrolyl; and m and n are each independently 0-2.

The compounds are said to be useful for the treatment of restenosis, immune disease, and diabetic complications.

Smith, et al., (*Bioorg. Med. Chem. Lett.* 5:2783-2788 (1995)) reported the anti-rheumatic potential of a series of 2,4-di-substituted-4H-naphtho[1,2-b]pyran-3-carbonitriles. They reported that 4-(3-nitrophenyl)-2-(N-succinimido)-4H-naphtho[1,2-b]pyran-3-carbonitrile has proved to be acid stable and still retains biological activity:

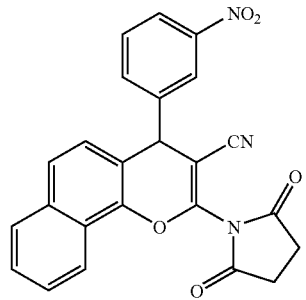

Birch, et al., (*Diabetes* 45:642-650 (1996)) reported that LY290181, an inhibitor of diabetes-induced vascular dysfunction, blocks protein kinase C-stimulated transcriptional activation through inhibition of transcription factor binding to a phorbol response element:

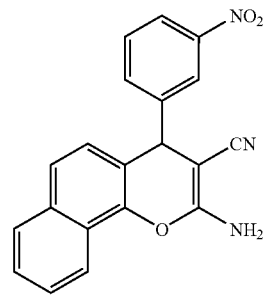

LY290181

Panda, et al., (*J. Biol. Chem.* 272: 7681-7687 (1997)) reported the suppression of microtubule dynamics by LY290181, which might be the potential mechanism for its antiproliferative action.

Wood, et al., (*Mol. Pharmacol.* 52: 437-444 (1997)) reported that LY290181 inhibited mitosis and microtubule function through direct tubulin binding.

PCT published patent application WO9824427 disclosed antimicrotubule compositions and methods for treating or preventing inflammatory diseases. LY290181 was listed as an antimicrotubule agent.

WO0134591 disclosed 4H-chromenes and analogs as activators of caspases and inducers of apoptosis:

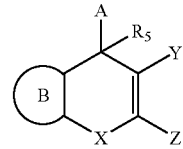

wherein,

X is O, S or NR₆, wherein R₆ is hydrogen or optionally substituted alkyl;

Y is CN, COR₇, CO₂R₇ or CONR$_x$R$_y$, wherein R₇, R$_x$ and R$_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl;

or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_5$ is hydrogen or $C_{1-10}$ alkyl;

A is optionally substituted and is aryl, heteroaryl, saturated carbocyclic, partially saturated carbocylic, saturated heterocyclic, partially saturated heterocyclic, arylalkyl or heteroarylalkyl; and B is an optionally substituted aromatic or heteroaromatic ring.

PCT published patent application WO02092076 disclosed substituted coumarins and quinolines and analogs as activators of caspases and inducers of apoptosis:

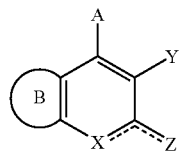

wherein, the dashed lines cannot both be a double bond at the same time;

X is O, S or $NR_6$, wherein $R_6$ is hydrogen or optionally substituted alkyl or aryl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is O, S, halo, $NR_8$, or $NCOR_8$, wherein $R_8$ is independently H, $C_{1-4}$ alkyl or aryl;

A is optionally substituted and is aryl, heteroaryl, saturated carbocyclic, partially saturated carbocyclic, saturated heterocyclic, partially saturated heterocyclic, arylalkyl or heteroarylalkyl; and B is optionally substituted and is an aryl, heteroaryl, saturated carbocyclic, partially saturated carbocyclic, saturated heterocyclic, or partially saturated heterocyclic ring.

PCT published patent application WO02092083 disclosed 7,8-fused 4H-chromene and analogs as activators of caspases and inducers of apoptosis:

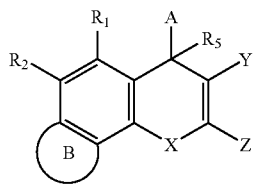

wherein,

X is O, S or $NR_6$, wherein $R_6$ is hydrogen or optionally substituted alkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_1$-$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocylic, saturated heterocyclic, partially saturated heterocyclic, arylalkyl or heteroarylalkyl; and B is optionally substituted and is a fused thiazole, oxazole, 2-imino-imidazole, 2,1,3-thiadiazo-2-one, thiazol-2-one, oxazol-2-one, imidazol-2-thione, thiazol-2-thione, oxazol-2-thione, imidazoline, oxazoline, thiazoline, triazole, oxazine, oxazine-2,3-dione, or piperazine ring.

PCT published patent application WO02092594 disclosed substituted 4H-chromenes and analogs as activators of caspases and inducers of apoptosis:

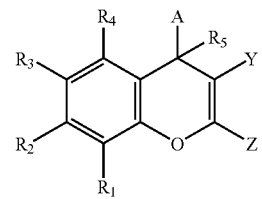

wherein, $R_1$-$R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached form an aryl, heteroaryl, partially saturated carbocyclic or partially saturated heterocyclic group, wherein said group is optionally substituted;

$R_5$ is hydrogen or $C_{1-10}$ alkyl;

A is optionally substituted and is aryl, heteroaryl, saturated carbocylic, partially saturated carbocylic, saturated heterocyclic, partially saturated heterocyclic or arylalkyl;

Y is CN, $COR_7$, $CO_2R_7$ or $CONR_xR_y$, wherein $R_7$, $R_x$ and $R_y$ are independently hydrogen, $C_{1-10}$ to alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle; and Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle.

SUMMARY OF THE INVENTION

The present invention is related to the discovery that substituted 4H-chromenes, 2H-chromenes, chromans and analogs, as represented in Formula I, are activators of the caspase cascade and inducers of apoptosis. Thus, an aspect of the present invention is directed to the use of compounds of Formula I as inducers of apoptosis.

A second aspect of the present invention is to provide a method for treating, preventing or ameliorating neoplasia and cancer by administering a compound of Formula I to a mammal in need of such treatment.

Many of the compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

DETAILED DESCRIPTION OF THE INVENTION

The present invention arises out of the discovery that substituted 4H-chromenes, 2H-chromenes, chromans and analogs, as represented in Formula I, are potent and highly efficacious activators of the caspase cascade and inducers of apoptosis. Therefore, compounds of Formula I are useful for treating disorders responsive to induction of apoptosis.

Specifically, compounds useful in this aspect of the present invention are represented by Formula I:

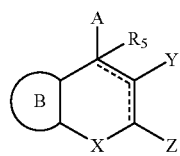

(I)

wherein $R_5$ is not present when the dotted line between carbon atoms bonded to groups A and Y is a double bond. Compounds useful in the invention are further represented by Formulae Ia and Ib:

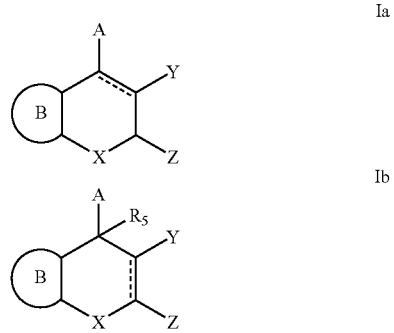

or pharmaceutically acceptable salts or prodrugs thereof, wherein:

X is O, S or $NR_6$, wherein $R_6$ is hydrogen or optionally substituted alkyl;

Y is H, halogen, CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is H, OH, $OR_8$, $OCOR_8$, wherein $R_8$ is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl;

$R_5$ is hydrogen or $C_{1-10}$ alkyl;

A is optionally substituted and is aryl, heteroaryl, saturated carbocyclic, partially saturated carbocylic, saturated heterocyclic, partially saturated heterocyclic, arylalkyl or heteroarylalkyl;

B is an optionally substituted aromatic, heteroaromatic or partially saturated heterocyclic ring;

the dotted lines are single or double bonds, provided that both sets of dotted lines can not be double bonds at the same time; and when Z is OH and a double bond is present between the carbon atoms bonded to groups Y and Z, it is understood that this is the enol form and is equivalent to the tautomeric keto form.

Preferred compounds of Formula I include compounds wherein A is phenyl, naphthyl, pyridyl, quinolyl, isoquinolyl, thienyl, furyl, pyrrolyl, indolyl, 2-phenylethyl or cyclohexyl, any of which is optionally substituted.

Preferably B is optionally substituted and selected from the group consisting of benzo, naphtho, indolo, isoindolo, benzimidazolo, benzimidazol-2-one, benzimidazol-2-thione, benzthiazolo, benzthiazol-e-one, benztiazol-2-thione, benzoxazolo, benzoxazol-2-one, benzoxazol-2-thione, benztriazolo, quinoxalino, quinoxalin-2-one, thienyl, benzothienly, furanyl, benzofuranyl, benzooxazine, benzooxazin-2,3-one, 2,3-dihydro-benzofuranyl, quino and isoquino. Preferably, $R_5$ is hydrogen. Preferably, X is O or S. Most preferably, X is O. Preferably, Y is CN or H. Preferably, Z is H, OH, OMe or $OCOCH_3$.

Optional substituents on B include, without limitation, alkyl, cycloalkylalkyl, hydroxylalkyl, epoxyalkyl, alkoxyalkyl, aminoalkyl and haloalkyl. Preferred optional substitutents on B include methyl, hydroxymethyl, cyclopropylmethyl and amino, including dimethylamino, ethylamino, and 2-N,N-diethylaminoethyl.

Preferred structures of Formula I are substituted 4H-chromenes and analogs represented by Formulae II-IV. In particular, a preferred embodiment is represented by Formula II:

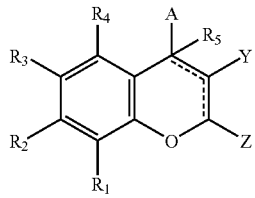

wherein $R_5$ is not present when the dotted line between carbon atoms bonded to groups A and Y is a double bond. Preferred compounds useful in the invention are further represented by Formulae IIa, IIb and IIc:

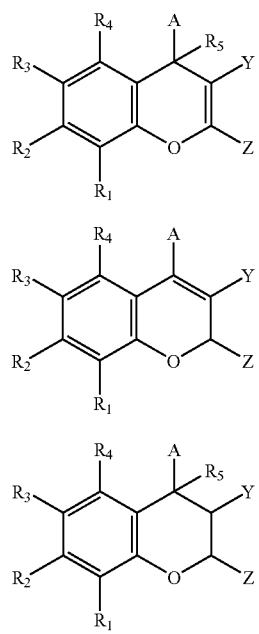

or pharmaceutically acceptable salts or prodrugs thereof, wherein:

$R_1$-$R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached to form an aryl, heteroaryl, partially saturated carbocyclic or partially saturated heterocyclic group, wherein said group is optionally substituted.

Preferably $R_1$ and $R_2$ are taken together with the atoms to which they are attached to form an aryl, heteroaryl, partially saturated carbocyclic or partially saturated heterocyclic group, wherein said group is optionally substituted.

Preferred are compounds of Formula II, wherein $R_1$ and $R_2$ are taken together to form a structure selected from the group consisting of —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(R)—CH═CH—, —CH═CH—N(R)—, —O—CH═CH—, —CH═CH—O—, —S—CH═CH—, —CH═CH—S—, —CH═CH—CH═CH—, —N═CH—CH═CH—, —CH═N—CH═CH—, —CH═CH—N═CH—, —CH═CH—CH═N—, —N═CH—CH═N—, —N═CH—N(R)—, —N(R)—CH═N—, —N(R)—C(═O)N(R$_{15}$)—, —N═CH—O—, —N(R)—C(═O)O—, —O—CH═N—, —O—C(═O)—N(R)—, —N═CH—S—, —N(R)—C(═O)S—, —S—CH═N—, —S—C(═O)—N(R)—, wherein R and $R_{15}$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferred compounds falling within the scope of Formula II include compounds wherein $R_3$ and $R_4$ are each hydrogen; more preferably $R_3$, $R_4$ and $R_5$ are each hydrogen. Preferred compounds of Formula II include compounds wherein A is phenyl, naphthyl, pyridyl, quinolyl, isoquinolyl, thienyl, furyl, pyrrolyl, indolyl, 2-phenylethyl, dihydrophenyl, tetrahydrophenyl or cyclohexyl, any of which is optionally substituted. More preferably, A is optionally substituted phenyl or optionally substituted pyridyl. Preferably, $R_5$ is hydrogen. Preferably, Y is CN or H. Preferably, Z is H, OH or OMe.

When Z is OH in Formula IIa, it is understood to one of ordinary skill in the art that the enol structure is equivalent to and/or a tautomer of the keto structure shown below.

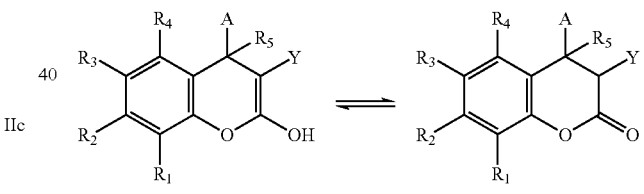

Another preferred embodiment is represented by Formula III:

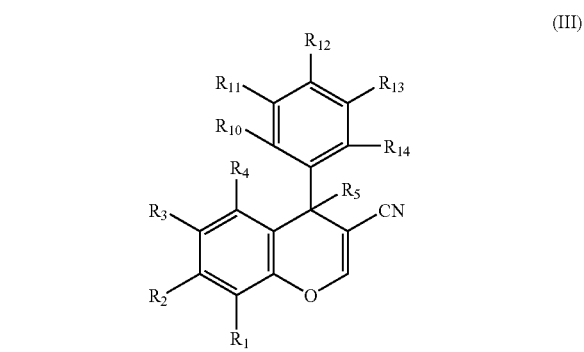

or pharmaceutically acceptable salts or prodrugs thereof, wherein $R_1$-$R_5$ are as defined previously with respect to Formula II; and $R_{10}$-$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached to form an aryl, heteroaryl, partially saturated carbocyclic or partially saturated heterocyclic group, wherein said group is optionally substituted.

Preferred are compounds of Formula III, wherein $R_{10}$ and $R_{11}$, or $R_{11}$ and $R_{12}$, taken together to form a structure selected from the group consisting of —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(R)—CH=CH—, —CH=CH—N(R)—, —O—CH=CH—, —CH=CH—O—, —S—CH=CH—, —CH=CH—S—, —CH=CH—CH=CH—, —N=CH—CH=CH—, —CH=N—CH=CH—, —CH=CH—N=CH—, —CH=CH—CH=N—, —N=CH—CH=N—, —N=CH—N(R)—, —N(R)—CH=N—, —N(R)—C(=O)N(R$_{15}$)—, —N=CH—O—, —N(R)—C(=O)O—, —O—CH=N—, —O—C(=O)—N(R)—, —N=CH—S—, —N(R)—C(=O)S—, —S—CH=N—, —S—C(=O)—N(R)—, wherein R and $R_{15}$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferred compounds falling within the scope of Formula III include compounds wherein $R_1$-$R_2$ are independently hydrogen, halogen, hydroxy, $C_{1-10}$ alkyl, hydroxyalkyl, aminoalkyl, carboxyalkyl, amino, acylamido, acyloxy, alkoxy, methylenedioxy or alkylthiol. Preferably $R_5$ is hydrogen.

Preferred compounds falling within the scope of Formula III include compounds wherein $R_1$ and $R_2$ are taken together with the atoms to which they are attached to form an aryl, heteroaryl, partially saturated carbocyclic or partially saturated heterocyclic group, wherein said group is optionally substituted.

Preferred are compounds of Formula III, wherein $R_1$ and $R_2$ are taken together to form a structure selected from the group consisting of —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(R)—CH=CH—, —CH=CH—N(R)—, —O—CH=CH—, —CH=CH—O—, —S—CH=CH—, —CH=CH—S—, —CH=CH—CH=CH—, —N=CH—CH=CH—, —CH=N—CH=CH—, —CH=CH—N=CH—, —CH=CH—CH=N—, —N=CH—CH=N—, —N=CH—N(R)—, —N(R)—CH=N—, —N(R)—C(=O)N(R$_{15}$)—, —N=CH—O—, —N(R)—C(=O)O—, —O—CH=N—, —O—C(=O)—N(R)—, —N=CH—S—, —N(R)—C(=O)S—, —S—CH=N—, —S—C(=O)—N(R)—, wherein R and $R_{15}$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Another preferred embodiment is represented by Formula IV:

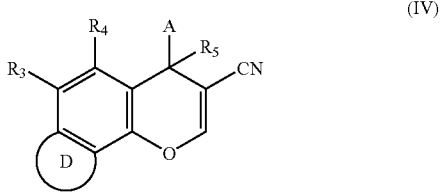

(IV)

or pharmaceutically acceptable salts or prodrugs thereof, wherein A and $R_3$-$R_5$ are as defined previously with respect to Formulae I and II; and D is an aryl, heteroaryl, partially saturated carbocyclic or partially saturated heterocyclic group, wherein said group is optionally substituted.

Preferred compounds falling within the scope of Formula IV include compounds wherein $R_3$-$R_4$ are hydrogen. Preferably $R_5$ is hydrogen. Preferably D is an optionally substituted aromatic or heteroaromatic ring selected from the group consisting of benzo, pyrido, furo, 2,3-dihydrofuryl, thieno, pyrrolo, 2,3-dihydropyrrolo, imidazo, imidazol-2-one, imidazol-2-thione, dioxolano, oxazolo, oxazol-2-one, oxazol-2-thione, thiazolo, thiazol-2-one, thiazol-2-thione, pyrazolo, pyrazo, pyrazin-2,3-dione and triazolo.

Another preferred embodiment is represented by Formula V:

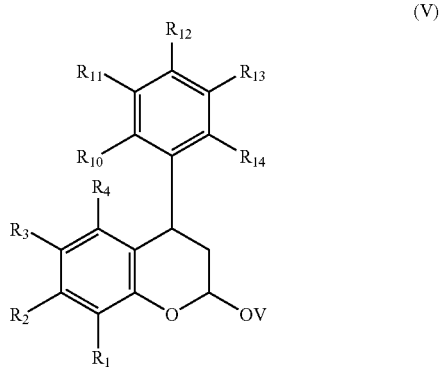

(V)

or pharmaceutically acceptable salts or prodrugs thereof, wherein:

V is H, $R_8$ or $COR_8$, where $R_8$ is as defined previously with respect to Formula I; and $R_1$-$R_4$ and $R_{10}$-$R_{14}$ are as defined previously with respect to Formulas II-III.

Exemplary preferred compounds that may be employed in the method of the invention include, without limitation:
4-(3-Bromo-4,5-dimethoxyphenyl)-3-cyano-7-dimethylamino-4H-chromene;
4-(3-Bromo-4,5-dimethoxyphenyl)-3-cyano-7-ethylamino-4H-chromene;
4-(3-Bromo-4,5-dimethoxyphenyl)-3-cyano-7-methoxy-4H-chromeme;
3-Cyano-4-(5-methyl-3-pyridyl)-4H-indolo[4,5-b]pyran;
4-(5-Bromo-3-pyridyl)-3-cyano-4H-indolo[4,5-b]pyran;
4-(3-Bromo-4,5-dimethoxyphenyl)-3-cyano-4H-indolo[4,5-b]pyran;

4-(3-Bromo-4,5-dimethoxyphenyl)-3-cyano-7-methyl-4H-indolo[4,5-b]pyran;
4-(3-Bromo-4-hydroxy-5-methoxyphenyl)-3-cyano-7-methyl-4H-indolo[4,5-b]pyran;
4-(3-Bromo-4,5-dimethoxyphenyl)-3-cyano-7-ethyl-4H-indolo[4,5-b]pyran;
3-Cyano-7-methyl-4-(5-methyl-3-pyridyl)-4H-indolo[4,5-b]pyran;
4-(5-Bromo-pyridin-3-yl)-3-cyano-7-methyl-4H-indolo[4,5-b]pyran;
3-Cyano-7-methyl-4-(5-methoxy-3-pyridyl)-4H-indolo[4,5-b]pyran;
4-(3-Bromo-4,5-dimethoxyphenyl)-3-cyano-4H-indolo[7,6-b]pyran;
3-Cyano-7-methyl-4-(3,4,5-trimethoxyphenyl)-4H-indolo[7,6-b]pyran;
4-(3-Bromo-4,5-dimethoxyphenyl)-3-cyano-4H-imidazo[4,5-h]chromene;
4-(3-Bromo-4,5-dimethoxyphenyl)-3-cyano-7-methyl-4H-imidazo[4,5-h]chromene;
4-(3-Bromo-4,5-dimethoxyphenyl)-3-cyano-7-methyl-8-oxo-4H-oxazolo[4,5-h]chromene;
4-(3-Bromo-4,5-dimethoxyphenyl)-3-cyano-4H-furo[2,3-h]chromene;
4-(3-Bromo-4,5-dimethoxyphenyl)-3-cyano-4H-thieno[2,3-h]chromene;
4-(3-Bromo-4,5-dimethoxyphenyl)-3-cyano-4H-pyrazo[2,3-h]chromene;
3-Cyano-7-methoxy-4-(3,4,5-trimethoxyphenyl)-4H-chromene;
3-Cyano-4-phenyl-4H-chromene;
7-Dimethylamino-4-(3,4,5-trimethoxyphenyl)-2H-chromene;
3-Chloro-7-dimethylamino-4-(3,4,5-trimethoxyphenyl)-2H-chromene;
3-Cyano-7-methoxy-4-(3,4,5-trimethoxyphenyl)-chroman;
4-(3-Bromo-4,5-dimethoxyphenyl)-3-cyano-2-hydroxy-pyrrolo[2,3-h]chroman;
4-(3-Bromo-4,5-dimethoxyphenyl)-3-cyano-2-oxo-pyrrolo[2,3-h]chroman;
3-Cyano-7-methoxy-2-oxo-4-(3,4,5-trimethoxyphenyl)-chroman
4-(3-Bromo-4,5-dimethoxyphenyl)-2-hydroxy-7-methyl-pyrrolo[2,3-h]chroman;
4-(3-Bromo-4,5-dimethoxyphenyl)-7-dimethylamino-2-hydroxy-chroman;
4-(3-Bromo-4,5-dimethoxyphenyl)-7-dimethylamino-2-methoxy-chroman;
2-Acetoxy-4-(3-Bromo-4,5-dimethoxyphenyl)-7-methyl-pyrrolo[2,3-h]chroman;
2-Acetoxy-4-(3-Bromo-4,5-dimethoxyphenyl)-7-dimethylamino-chroman;
2,2-Dimethyl-4-(3-methoxyphenyl)-7-methoxy-2H-chromene;
3-Bromo-2,2-dimethyl-4-(3-methoxyphenyl)-7-methoxy-2H-chromene;
2-(3-Aminopropoxy)-4-(3,4-dimethoxypheny)-7-dimethylamino-chroman;
4-(3-Bromo-4,5-dimethoxyphenyl)-7-dimethylamino-chroman;
4-(3-Bromo-4,5-dimethoxyphenyl)-2-methoxy-7-methyl-pyrrolo[2,3-h]chroman;
4-(3-Bromo-4,5-dimethoxyphenyl)-7-methyl-pyrrolo[2,3-h]chroman-2-one;
4-(3-Bromo-4,5-dimethoxyphenyl)-7-methyl-pyrrolo[2,3-h]chroman;
7-Methoxy-2-hydroxy-4-(3,4,5-trimethoxyphenyl)-chroman;
4-(3-Bromo-4,5-dimethoxyphenyl)-2-hydroxy-pyrrolo[2,3-h]chroman;
2-Hydroxy-7-methyl-4-(3,4,5-trimethoxyphenyl)-pyrrolo[2,3-h]chroman;
4-(3-Bromo-4,5-dimethoxyphenyl)-2-hydroxy-pyrido[3,4-h]chroman;
N-[4-(3-Bromo-4,5-dimethoxyphenyl)-2-hydroxy-chroman-7-yl]-acetamide;
4-(3-Bromo-4,5-dimethoxyphenyl)-2-hydroxy-pyrido[3,2-h]chroman;
4-(3-Bromo-4,5-dimethoxyphenyl)-7,9-dihydro-2-hydroxy-8-oxo-imidazolo[4,5-h]chroman;
4-(3-Bromo-4,5-dimethoxyphenyl)-2-hydroxy-pyrrolo[3,2-h]chroman;
7-Methoxy-4-(3,4,5-trimethoxyphenyl)-chroman-2-one;
4-(3-Hydroxy-4-methoxyphenyl)-6,7,8-trimethoxy-chroman-2-one;
2-(3-Aminopropoxy)-3-bromo-4-(3,4-dimethoxypheny)-7-dimethylamino-chroman;
2-(3-Aminopropoxy)-7-methoxy-4-(3,4,5-trimethoxypheny)-chroman;
4-(3,5-Dichlorophenyl)-2-hydroxy-pyrido[3,4-h]chroman;
4-(4-Methoxyphenyl)-5,6,7-trimethoxy-chroman-2-one;
4-(3,4-Dimethoxyphenyl)-5,6,7-trimethoxy-chroman-2-one;
4-(3,5-Dichlorophenyl)-2-hydroxy-pyrrolo[2,3-h]chroman;
7-Amino-4-(3-bromo-4,5-dimethoxyphenyl)-2-methoxy-chroman;
7-Amino-4-(3,5-Dichlorophenyl)-2-methoxy-chroman;
4-(4-Methoxyphenyl)-6,7,8-trimethoxy-chroman-2-one;
N-[4-(3,5-Dichlorophenyl)-2-hydroxy-chroman-7-yl]-acetamide; and pharmaceutically acceptable salts or prodrugs thereof.

The present invention is also directed to novel compounds within the scope of Formulae I-IV:

4-(3-Bromo-4,5-dimethoxyphenyl)-3-cyano-7-dimethylamino-4H-chromene;
4-(3-Bromo-4,5-dimethoxyphenyl)-3-cyano-7-ethylamino-4H-chromene;
4-(3-Bromo-4,5-dimethoxyphenyl)-3-cyano-7-methoxy-4H-chromeme;
3-Cyano-4-(5-methyl-3-pyridyl)-4H-indolo[4,5-b]pyran;
4-(5-Bromo-3-pyridyl)-3-cyano-4H-indolo[4,5-b]pyran;
4-(3-Bromo-4,5-dimethoxyphenyl)-3-cyano-4H-indolo[4,5-b]pyran;
4-(3-Bromo-4,5-dimethoxyphenyl)-3-cyano-7-methyl-4H-indolo[4,5-b]pyran;
4-(3-Bromo-4-hydroxy-5-methoxyphenyl)-3-cyano-7-methyl-4H-indolo[4,5-b]pyran;
4-(3-Bromo-4,5-dimethoxyphenyl)-3-cyano-7-ethyl-4H-indolo[4,5-b]pyran;
3-Cyano-7-methyl-4-(5-methyl-3-pyridyl)-4H-indolo[4,5-b]pyran;
4-(5-Bromo-3-pyridyl)-3-cyano-7-methyl-4H-indolo[4,5-b]pyran;
3-Cyano-7-methyl-4-(5-methoxy-3-pyridyl)-4H-indolo[4,5-b]pyran;
4-(3-Bromo-4,5-dimethoxyphenyl)-3-cyano-4H-indolo[7,6-b]pyran;
3-Cyano-7-methyl-4-(3,4,5-trimethoxyphenyl)-4H-indolo[7,6-b]pyran;
4-(3-Bromo-4,5-dimethoxyphenyl)-3-cyano-4H-imidazo[4,5-h]chromene;

4-(3-Bromo-4,5-dimethoxyphenyl)-3-cyano-7-methyl-4H-imidazo[4,5-h]chromene;
4-(3-Bromo-4,5-dimethoxyphenyl)-3-cyano-7-methyl-8-oxo-4H-oxazolo[4,5-h]chromene;
4-(3-Bromo-4,5-dimethoxyphenyl)-3-cyano-4H-furo[2,3-h]chromene;
4-(3-Bromo-4,5-dimethoxyphenyl)-3-cyano-4H-thieno[2,3-h]chromene;
4-(3-Bromo-4,5-dimethoxyphenyl)-3-cyano-4H-pyrazo[2,3-h]chromene;
3-Cyano-7-methoxy-4-(3,4,5-trimethoxyphenyl)-4H-chromene;
3-Cyano-4-phenyl-4H-chromene;
7-Dimethylamino-4-(3,4,5-trimethoxyphenyl)-2H-chromene;
3-Chloro-7-dimethylamino-4-(3,4,5-trimethoxyphenyl)-2H-chromene;
3-Cyano-7-methoxy-4-(3,4,5-trimethoxyphenyl)-chroman;
4-(3-Bromo-4,5-dimethoxyphenyl)-3-cyano-2-hydroxy-pyrrolo[2,3-h]chroman;
4-(3-Bromo-4,5-dimethoxyphenyl)-3-cyano-2-oxo-pyrrolo[2,3-h]chroman;
3-Cyano-7-methoxy-2-oxo-4-(3,4,5-trimethoxyphenyl)-chroman
4-(3-Bromo-4,5-dimethoxyphenyl)-2-hydroxy-7-methyl-pyrrolo[2,3-h]chroman;
4-(3-Bromo-4,5-dimethoxyphenyl)-7-dimethylamino-2-hydroxy-chroman;
4-(3-Bromo-4,5-dimethoxyphenyl)-7-dimethylamino-2-methoxy-chroman;
2-Acetoxy-4-(3-Bromo-4,5-dimethoxyphenyl)-7-methyl-pyrrolo[2,3-h]chroman;
2-Acetoxy-4-(3-Bromo-4,5-dimethoxyphenyl)-7-dimethylamino-chroman;
2,2-Dimethyl-4-(3-methoxyphenyl)-7-methoxy-2H-chromene;
3-Bromo-2,2-dimethyl-4-(3-methoxyphenyl)-7-methoxy-2H-chromene;
2-(3-Aminopropoxy)-4-(3,4-dimethoxypheny)-7-dimethylamino-chroman;
4-(3-Bromo-4,5-dimethoxyphenyl)-7-dimethylamino-chroman;
4-(3-Bromo-4,5-dimethoxyphenyl)-2-methoxy-7-methyl-pyrrolo[2,3-h]chroman;
4-(3-Bromo-4,5-dimethoxyphenyl)-7-methyl-pyrrolo[2,3-h]chroman-2-one;
4-(3-Bromo-4,5-dimethoxyphenyl)-7-methyl-pyrrolo[2,3-h]chroman;
7-Methoxy-2-hydroxy-4-(3,4,5-trimethoxyphenyl)-chroman;
4-(3-Bromo-4,5-dimethoxyphenyl)-2-hydroxy-pyrrolo[2,3-h]chroman;
2-Hydroxy-7-methyl-4-(3,4,5-trimethoxyphenyl)-pyrrolo[2,3-h]chroman;
4-(3-Bromo-4,5-dimethoxyphenyl)-2-hydroxy-pyrido[3,4-h]chroman;
N-[4-(3-Bromo-4,5-dimethoxyphenyl)-2-hydroxy-chroman-7-yl]-acetamide;
4-(3-Bromo-4,5-dimethoxyphenyl)-2-hydroxy-pyrido[3,2-h]chroman;
4-(3-Bromo-4,5-dimethoxyphenyl)-7,9-dihydro-2-hydroxy-8-oxo-imidazolo[4,5-h]chroman;
4-(3-Bromo-4,5-dimethoxyphenyl)-2-hydroxy-pyrrolo[3,2-h]chroman;
7-Methoxy-4-(3,4,5-trimethoxyphenyl)-chroman-2-one;
4-(3-Hydroxy-4-methoxyphenyl)-6,7,8-trimethoxy-chroman-2-one;
2-(3-Aminopropoxy)-3-bromo-4-(3,4-dimethoxypheny)-7-dimethylamino-chroman;
2-(3-Aminopropoxy)-7-methoxy-4-(3,4,5-trimethoxypheny)-chroman;
4-(3,5-Dichlorophenyl)-2-hydroxy-pyrido[3,4-h]chroman;
4-(4-Methoxyphenyl)-5,6,7-trimethoxy-chroman-2-one;
4-(3,4-Dimethoxyphenyl)-5,6,7-trimethoxy-chroman-2-one;
4-(3,5-Dichlorophenyl)-2-hydroxy-pyrrolo[2,3-h]chroman;
7-Amino-4-(3-bromo-4,5-dimethoxyphenyl)-2-methoxy-chroman;
7-Amino-4-(3,5-Dichlorophenyl)-2-methoxy-chroman;
4-(4-Methoxyphenyl)-6,7,8-trimethoxy-chroman-2-one;
N-[4-(3,5-Dichlorophenyl)-2-hydroxy-chroman-7-yl]-acetamide; and pharmaceutically acceptable salts or prodrugs thereof.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group can be optionally substituted.

Optional substituents on the alkyl groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl. Optional substituents on the aryl, aralkyl and heteroaryl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy or carboxy.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylalkyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluoro-benzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

Useful saturated or partially saturated heterocyclic groups include oxazolonyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include benzooxazolonyl, benzooxazole-2-onyl, thienyl, benzo[b]thienyl, naphtho[2,3-b]thienyl, thianthrenyl, furyl, benzofuranyl, 2,3-dihydrobenzofuranyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, benzimidazol-2-one, benzimidazol-2-thione, 2-oxoindolyl, oxazolyl, oxazol-2-one and oxazol-2-thione. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Certain compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides, or phosphate according to methods known in the art); imines of amino containing compounds (e.g., those obtained by condensation with a $C_{1-4}$ aldehyde or ketone according to methods known in the art); carbamate of amino containing compounds, such as those described by Leu, et. al., (J. Med. Chem. 42:3623-3628 (1999)) and Greenwald, et. al., (J. Med. Chem. 42:3657-3667 (1999)); and acetals and ketals of alcohol containing compounds (e.g., those obtained by condensation with chloromethyl methyl ether or chloromethyl ethyl ether according to methods known in the art); and phosphonato and phosphono compounds (e.g., those obtained by condensation with a phosphate ester, phosphoryl chloride, or phosphoric acid), which include pharmaceutically acceptable mono-basic and di-basic addition salts of the phosphono group, e.g., organic bases, such as amine bases, which include ammonia, piperidine and morpholine.

The compounds of this invention may be prepared using methods known to those skilled in the art, or the novel methods of this invention. Specifically, the compounds of this invention with Formulae I-IV can be prepared as illustrated by exemplary reaction in Scheme 1. Substituted 2-amino chromenes can be prepared from reaction of a phenol with a benzaldehyde and malononitrile in the presence piperidine as described in WO0134591. Diazotization of 2-amino chromene using t-BuNO$_2$ in THF converted the 2-amino group into a diazonium group, followed by reduction using NaBH$_4$ to yield the 2-hydro chromene.

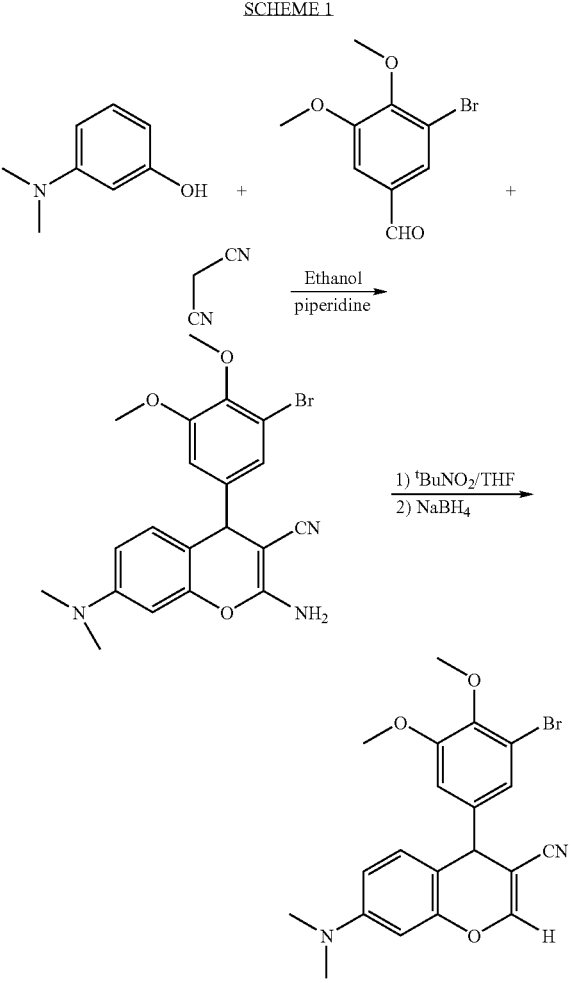

Compounds of this invention with Formulae I-IV can also be prepared as illustrated by exemplary reaction in Scheme 2. Reaction of 4-hydroxyindole with a substituted benzaldehyde and malononitrile in the presence of piperidine produced the indolo-pyran as described in WO0134591. Diazotization of the 2-amino compound using t-BuNO$_2$ in THF converted the 2-amino group into a diazonium group, which was reduced by NaBH$_4$ to yield the 2-hydro compound. Reaction of the compound with MeI or EtBr in the presence of a base, such as Cs$_2$CO$_3$ produced the 7-Me and 7-Et products.

Reaction of 1-methyl-4-hydroxyindole with a substituted arylaldehyde, such as 5-bromo-pyridine-3-carbaldehyde and malononitrile in the presence of piperidine, produced the indolo-pyran. Diazotization of the compound using t-BuNO$_2$ in THF converted the 2-amino group into a diazonium group, which was reduced by NaBH$_4$ to yield the 2-hydro product.

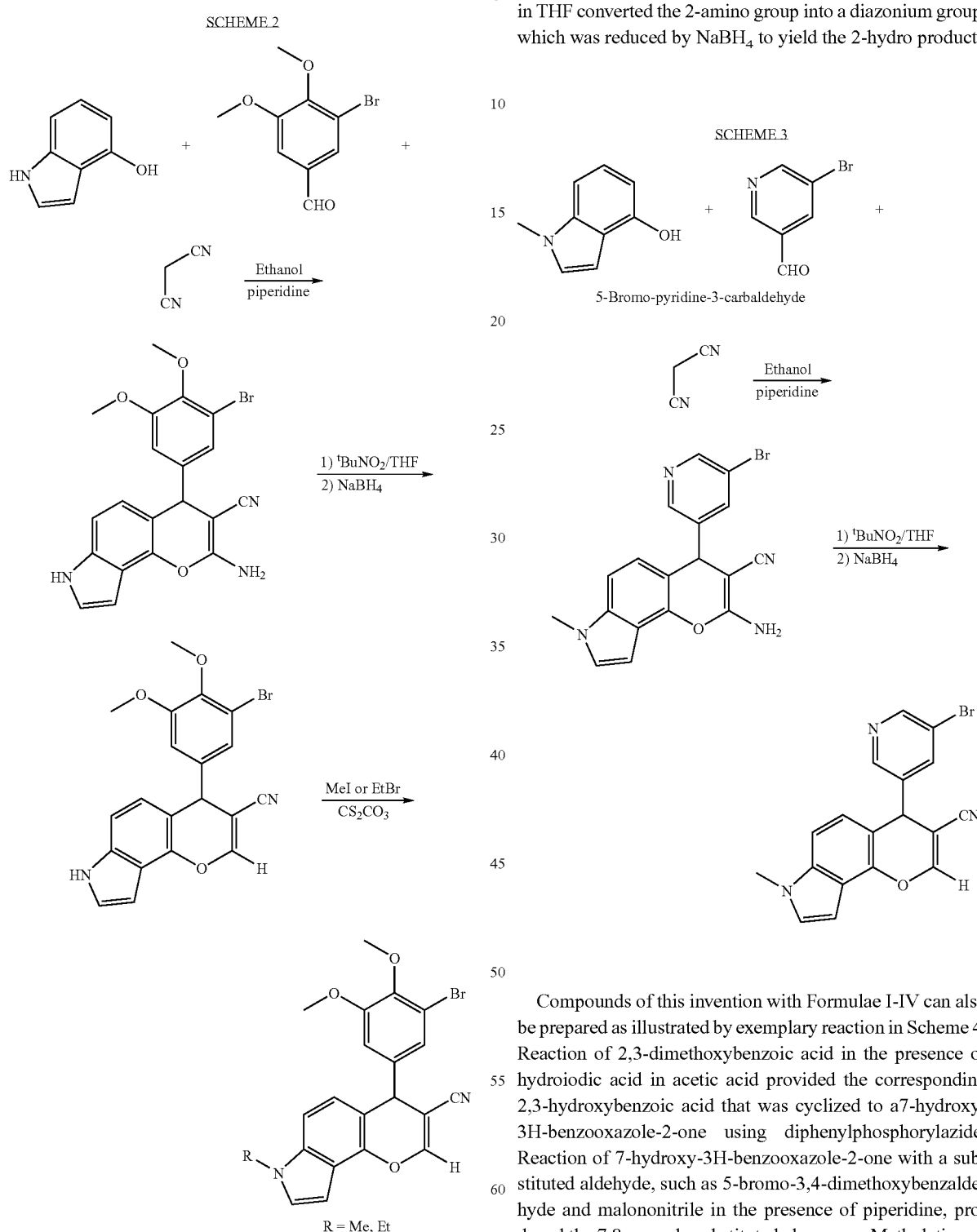

Compounds of this invention with Formulae I-IV can also be prepared as illustrated by exemplary reaction in Scheme 3.

Compounds of this invention with Formulae I-IV can also be prepared as illustrated by exemplary reaction in Scheme 4. Reaction of 2,3-dimethoxybenzoic acid in the presence of hydroiodic acid in acetic acid provided the corresponding 2,3-hydroxybenzoic acid that was cyclized to a 7-hydroxy-3H-benzooxazole-2-one using diphenylphosphorylazide. Reaction of 7-hydroxy-3H-benzooxazole-2-one with a substituted aldehyde, such as 5-bromo-3,4-dimethoxybenzaldehyde and malononitrile in the presence of piperidine, produced the 7,8-oxazole substituted chromene. Methylation of the compound with methyliodide and cesium carbonate, followed by diazotization of the compound using t-BuNO$_2$ in THF, converted the 2-amino group into a diazonium group, which was reduced by NaBH$_4$ to yield the 2-hydro product.

SCHEME 4

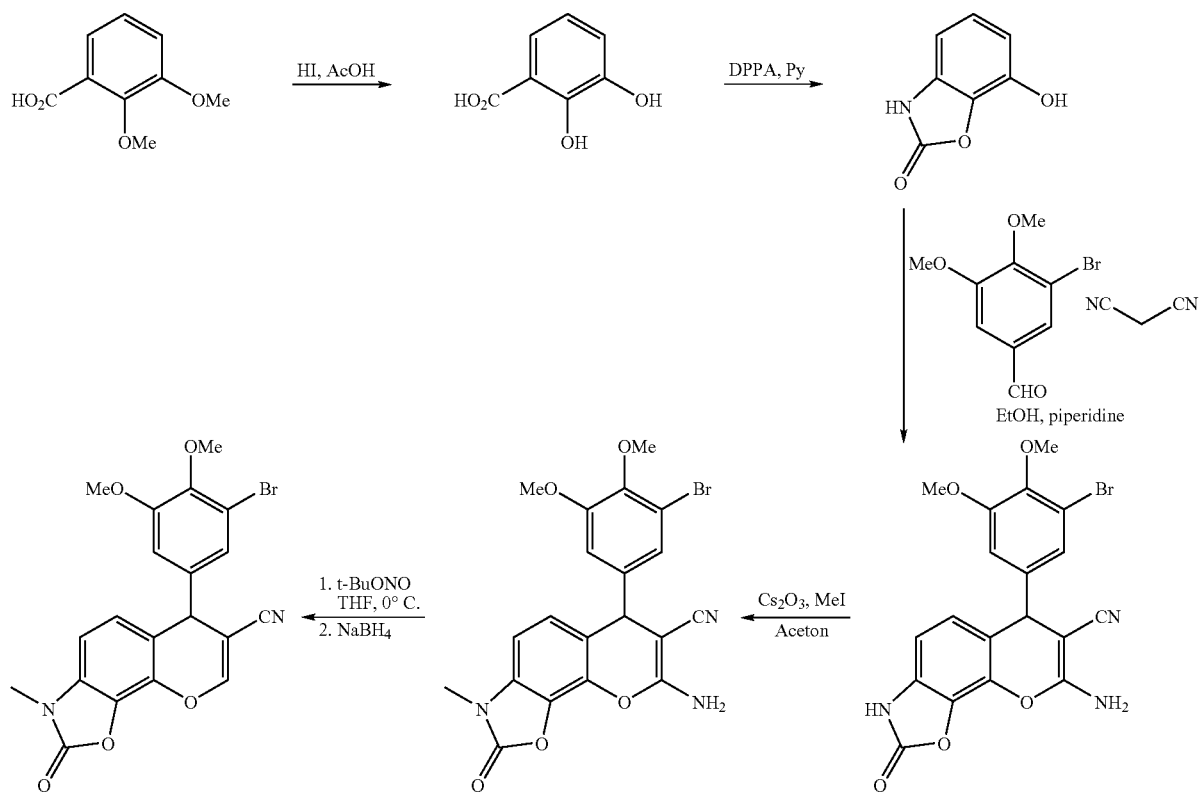

Compounds of this invention having the Formulae I-IV can also be prepared as illustrated by examplary reactions in Scheme V. A phenyl propionitrile is prepared from the condensation of acrylonitrile and dimethylaminophenol. The nitrile was hydrolysed to the acid and the intermediate compound cyclized to yield 7-dimethylamino-chroman-4-one. Trimethoxyiodobenzene was lithiated with butyl lithium and treated with 7-dimethylamino-chroman-4-one to produce dimethyl-[4-(3,4,5-trimethoxy-phenyl)-2H-chromen-7-yl]-amine. Alternatively, 7-dimethylamino-chroman-4-one could be first treated with copper chloride, followed by the addition of lithio trimethoxybenzene, to produce [3-chloro-4-(3,4,5-trimethoxy-phenyl)-2H-chromen-7-yl]-dimethyl-amine.

SCHEME 5

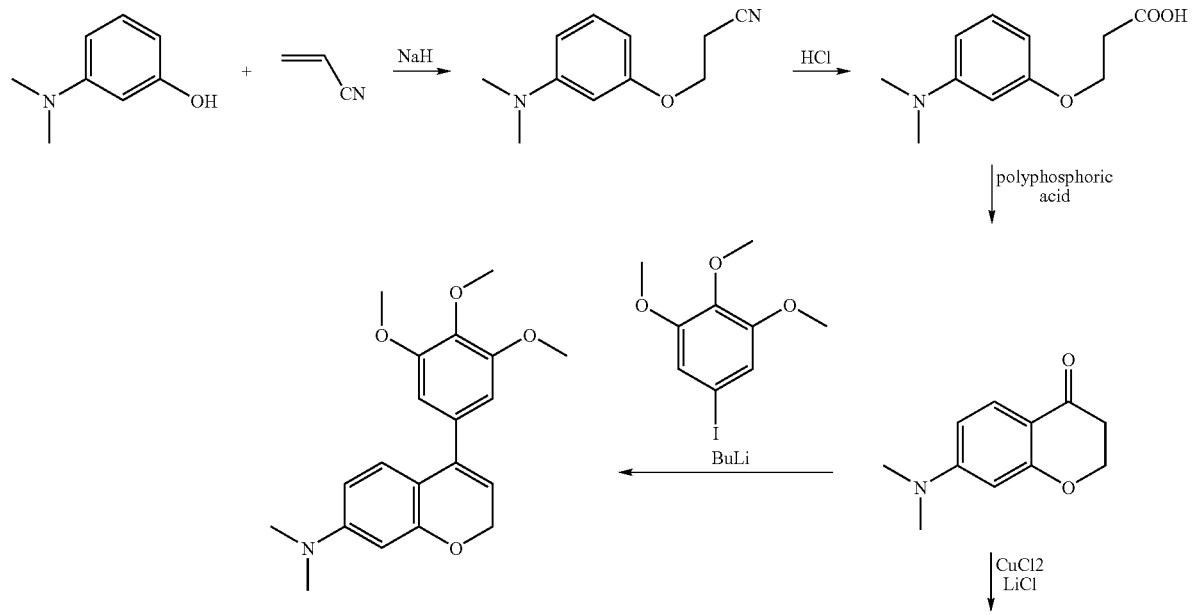

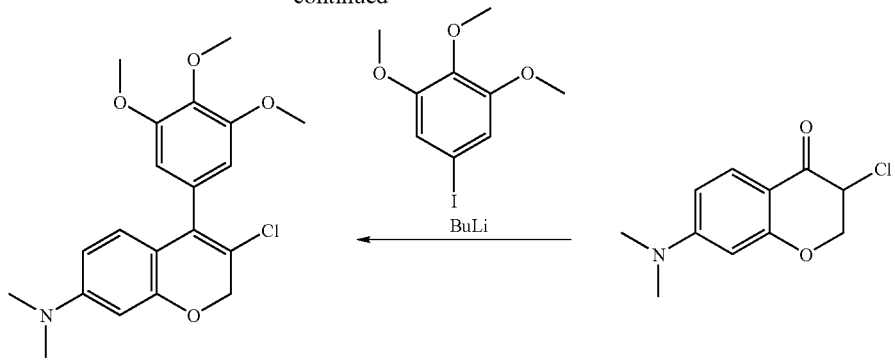

Compounds of this invention having the Formulae I-IV can also be prepared as illustrated by exemplary reactions in Scheme 6. Reaction of 3-bromo-4,5-dimethoxybenzaldehyde and 3,3-dimethoxypropionitrile in the presence of a base, such as sodium ethoxide, produced the substituted acrylonitrile. Treatment of the product with acid, such as HCl/H$_2$O, produced the substituted acrylonitrile-aldehyde. Reaction of the acrylonitrile-aldehyde with a substituted phenol, such as 4-hydroxyindole, in the presence of a base, such as piperidine, produced the substituted chroman product.

SCHEME 6

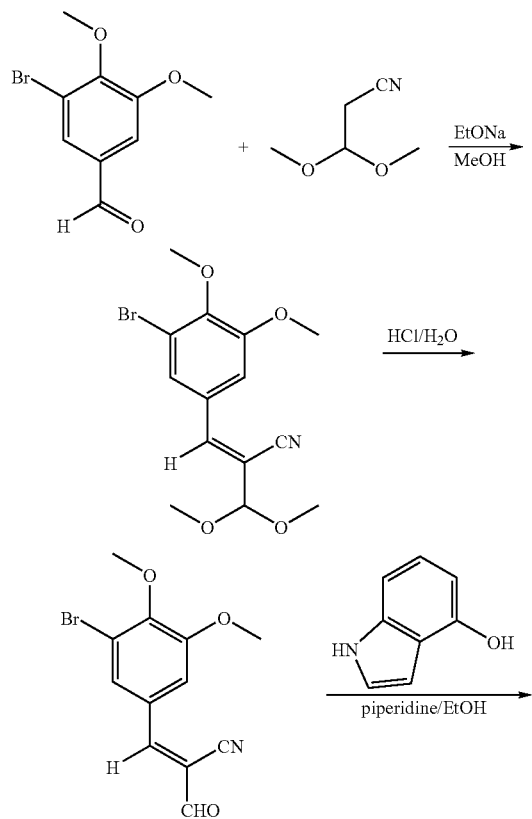

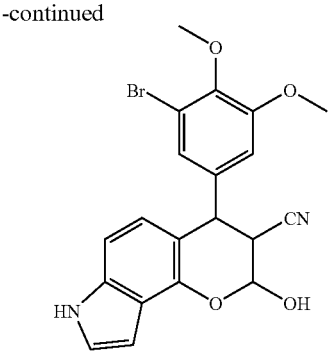

An important aspect of the present invention is the discovery that compounds having Formulae I-IV are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I-IV are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-IV, which functions as a caspase cascade activator and inducer of apoptosis.

The present invention also includes a therapeutic method comprising administering to an animal an effective amount of a compound, or a pharmaceutically acceptable salt or prodrug of said compound of Formulae I-IV, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphotic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinomas, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms In another embodiment, a pharmaceutical composition comprising a compound, or a pharmaceutically acceptable salt of said compound of Formulae I-IV, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-IV, which functions as a caspase cascade activator and inducer of apoptosis, in combination with at least one known cancer chemotherapeutic agent, or a pharmaceutically acceptable salt of said agent. Examples of known anti-cancer agents, which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from the at least one known cancer chemotherapeutic agent. In one embodiment, the compound of the invention and the at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugate of said compound of Formulae I-IV, which functions as a caspase cascade activator and inducer of apoptosis, in bioconjugation with at least one known therapeutically useful antibodies, such as Herceptin® or Rituxan®; growth factors, such as DGF, NGF; cytokines, such as IL-2, IL-4; or any molecule that binds to cell surface. The antibodies and other molecules will deliver compound of Formulae I-IV to its targets and make them effective anticancer agents. The bioconjugates also could enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of said compound of Formulae I-IV, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I-IV, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, and both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-III, which functions as a caspase cascade activator and inducer of apoptosis, is an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed.* 15:22-27 (1999), reported that lymphocytes treated with psoralen 8-MOP or TMP plus UVA displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of the compound of Formulae I-III, which functions as a caspase cascade activator and inducer of apoptosis, is an effective treatment for hyperproliferative diseases such as psoriasis.

Synovial cell hyperplasia is a characteristic of patients with rheumatoid arthritis (RA). Excessive proliferation of RA synovial cells, as well as defective in synovial cell death, might be responsible for the synovial cell hyperplasia. Wakisaka, et al., *Clin. Exp. Immunol.* 114:119-128 (1998), found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-III, which functions as a caspase cascade activator and inducer of apoptosis, is an effective treatment for rheumatoid arthritis.

There have been accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-III, which functions as a caspase cascade activator and inducer of apoptosis, is an effective treatment for inflammation and inflammatory bowel disease.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day, of the body weight of the mammal being treated for apoptosis-mediated disorders. Preferably, approximately 0.01 to approximately 10 mg/kg is orally administered to treat or prevent such disorders. For intramuscular injection, the dose is generally approximately one-half of the oral dose. For example, a suitable intramuscular dose would be approximately 0.0025 to approximately 25 mg/kg, and most preferably, from approximately 0.01 to approximately 5 mg/kg. If a known cancer chemotherapeutic agent is also administered, it is administered in an amount with is effective to achieve its intended purpose. The amounts of such known cancer chemotherapeutic agents effective for cancer are well known to those of skill in the art.

The unit oral dose may be comprised of approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from approximately 0.01 to 99%, preferably from approximately 0.25 to 75% of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, e.g. lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer such as glycerol or sorbitol. The push-fit capsules can contain the active compounds in the form of granules which may be mixed with fillers, such as lactose; binders, such as starches; and/or lubricants, such as talc or magnesium stearate and; optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400) or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil with warm soft paraffin, and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

4-(3-Bromo-4,5-dimethoxyphenyl)-3-cyano-4H-indolo[4,5-b]pyran

To a solution of 2-amino-4-(3-bromo-4,5-dimethoxy-phenyl)-3-cyano-4H-indolo[4,5-b]pyran (0.998 g, 2.34 mmol) in anhydrous THF (40 mL) kept at −30° C., was added tert-butylnitrite (1.0 mL, 7.58 mmol) via a syringe under argon. The light yellow solution was stirred between −20 to −10° C. for 4 h, then allowed to warm up to 0° C. The reaction mixture was cooled to −10° C. and sodium borohydride ($NaBH_4$, 0.259 g, 6.84 mmol) was added in one portion. The reaction mixture was warmed up to room temperature slowly and stirred overnight (15 h). The THF solvent was evaporated and the residue was dissolved in EtOAc (100 mL). The mixture was washed with saturated $NaHCO_3$ (15 mL) and brine (15 mL), dried over $MgSO_4$, and evaporated to yield a brown residue. The residue was purified by flash column chromatography (silica gel, EtOAc:hexanes/1:2) to yield 0.390 g (40%) of the product as an off-white solid. $^1H$ NMR ($CDCl_3$): 8.30 (brs, 1H), 7.45 (d, J=0.6 Hz, 1H), 7.24 (t, J=2.7 Hz, 1H), 7.13 (dd, J=0.8, 8.6 Hz, 1H), 6.96 (d, J=2.1 Hz, 1H), 6.76 (d, J=1.8 Hz, 1H), 6.70 (J=8.1 Hz, 1H), 6.67 (m, 1H), 4.81 (s, 1H), 3.84 (s, 3H), 3.83 (s, 3H).

EXAMPLE 2

4-(3-Bromo-4,5-dimethoxyphenyl)-3-cyano-7-dimethylamino-4H-chromene

To a solution of 2-amino-4-(3-bromo-4,5-dimethoxy-phenyl)-3-cyano-7-dimethylamino-4H-chromene (101 mg, 0.239 mmol) in anhydrous THF (5 mL) at 0° C., was added tert-butylnitrite (0.1 mL, 0.76 mmol) via a syringe under argon. The brown solution was stirred at 0° C. for 2.5 h. Sodium borohydride (20 mg, 0.52 mmol) was added in one portion. The reaction mixture was warmed up to room temperature slowly and stirred overnight. It was quenched with addition of water (5 mL), and extracted with EtOAc (2×15 mL). The EtOAc solution was washed with brine (5 mL), dried over $MgSO_4$, and evaporated to yield a brown residue. The residue was purified by flash column chromatography (silica gel, EtOAc:hexanes, 1:4) to yield 9 mg (9%) of the product as an off-white solid $^1H$ NMR ($CDCl_3$): 8.30 (d, J=1.2 Hz, 1H), 6.93 (d, J=2.1 Hz, 1H), 7.76 (dd, J=0.6, 8.7 Hz, 1H), 6.72 (d, J=1.8 Hz, 1H), 6.45 (dd, J=2.4, 8.7 Hz, 1H), 6.30 (d, J=2.7 Hz, 1H), 4.60 (s, 1H), 3.85 (s, 3H), 3.84 (s, 3H), 2.95 (s, 6H).

EXAMPLE 3

4-(5-Bromo-pyridin-3-yl)-3-cyano-7-methyl-4H-indolo[4,5-b]pyran

The title compound was prepared from of 2-amino-4-(5-bromo-pyridin-3-yl)-3-cyano-7-methyl-4H-indolo[4,5-b]pyran by a procedure similar to that described in Example 1 in 5% yield. $^1H$ NMR ($CDCl_3$): 8.59 (d, J=2.1 Hz, 1H), 8.50 (d, J=2.1 Hz, 1H), 7.64 (t, J=2.1 Hz, 1H), 7.49 (d, J=0.6 Hz, 1H), 7.09 (d, J=3.0 Hz, 1H), 7.07 (dd, J=0.9, 8.4 Hz, 1H), 6.65 (d, J=8.4 Hz, 1H), 6.60 (dd, J=0.9, 3.0 Hz, 1H), 4.94 (s, 1H), 3.79 (s, 3H).

EXAMPLE 4

4-(3-Bromo-4,5-dimethoxyphenyl)-3-cyano-7-methyl-4H-indolo[4,5-b]pyran

A mixture of 4-(3-bromo-4,5-dimethoxy-phenyl)-3-cyano-4H-indolo[4,5-b]pyran (51 mg, 0.124 mmol), iodomethane (23 μL, 0.370 mmol) and cesium carbonate (120 mg, 0.368 mmol) in acetone (2 mL) was stirred at room temperature in a sealed tube. After stirring at room temperature for 2.5 days, the reaction was diluted with EtOAc (20 mL). The insoluble material was filtered, and washed with EtOAc (30 mL). The EtOAc solution were combined, washed with brine (2×5 mL), dried over $MgSO_4$, and evaporated to yield an off-white solid. The crude product was purified by column chromatography (silica gel, EtOAc:hexanes, 1:1) to yield 51 mg (97%) of an off-white solid. $^1H$ NMR ($CDCl_3$): 7.43 (d, J=0.6 Hz, 1H), 7.07 (d, J=3.3 Hz, 1H), 7.05 (dd, J=0.6, 8.4 Hz, 1H), 6.95 (d, J=2.1 Hz, 1H), 6.76 (d, J=2.4 Hz, 1H), 6.72 (d, J=8.4 Hz, 1H), 6.58 (dd, J=0.6, 3.3 Hz, 1H), 4.81 (s, 1H), 3.84 (s, 3H), 3.82 (s, 3H), 3.78 (s, 3H).

EXAMPLE 5

4-(3-Bromo-4,5-dimethoxyphenyl)-3-cyano-7-ethyl-4H-indolo[4,5-b]pyran

A mixture of 4-(3-bromo-4,5-dimethoxy-phenyl)-3-cyano-4H-indolo[4,5-b]pyran (50 mg, 0.122 mmol), bromoethane (50 μL, 0.670 mmol) and cesium carbonate (122 mg, 0.375 mmol) in anhydrous THF (2 mL) was stirred at 60° C. in a sealed tube. After 22 h, additional bromoethane (100 μL, 1.34 mmol) was added and the reaction was continued for additional 43 h. The reaction mixture was diluted with EtOAc (20 mL). The insoluble material was filtered, and washed with EtOAc (30 mL). The EtOAc solution were combined, washed with brine (2×5 mL), dried over $MgSO_4$, and evaporated to yield a light yellow solid. The crude product was purified by column chromatography (silica gel, EtOAc:hexanes, 1:3) to yield 27 mg (51%) of the product as an off-white solid. $^1H$ NMR ($CDCl_3$) 7.44 (d, J=0.9 Hz, 1H), 7.14 (d, J=3.3 Hz, 1H), 7.07 (dd, J=0.6, 8.4 Hz, 1H), 6.96 (d, J=1.8 Hz, 1H), 6.77 (d, J=1.8 Hz, 1H), 6.70 (d, J=8.4 Hz, 1H), 6.59 (dd, J=0.9, 3.3 Hz, 1H), 4.81 (s, 1H), 4.15 (q, J=7.2 Hz, 2H), 3.84 (s, 3H), 3.83 (s, 3H), 1.46 (t, J=7.2 Hz, 3H).

EXAMPLE 6

3-Cyano-4-phenyl-4H-chromene

To a three-neck RB flask equipped with a thermometer and a condenser containing anhydrous DMF (1 mL) at 65° C. was added tert-butylnitrite (0.4 mL, 3.02 mmol), followed by slow addition of 3-cyano-2,7-diamino-4-phenyl-4H-chromene (263 mg, 1.0 mmol) in anhydrous DMF (1 mL) in 10 min. The reaction was stirred further for 5 min, then quenched with addition of water (10 mL). The mixture was extracted with EtOAc (3×10 mL). The EtOAc was washed with water (5 mL), brine (5 mL), dried over MgSO$_4$, and evaporated. The red residue was purified by chromatography on silica gel with EtOAc and hexane (1:4) as eluant to yield 64 mg (26%) of the product as an off-white solid. $^1$H NMR (CDCl$_3$): 7.4-7.18 (m, 7H), 7.07-7.01 (m, 2H), 6.96-6.62 (m, 1H), 4.77 (s, 1H).

EXAMPLE 7

4-(3-Bromo-4,5-dimethoxyphenyl)-3-cyano-7-methyl-8-oxo-4H-oxazolo[4,5-h]chromene Step 1

2,3-Dimethoxybenzoic acid (2 g, 10.98 mmol) was dissolved in acetic acid (25 mL). Hydroiodic acid solution (25 mL, 47% in water) was added and the reaction stirred under reflux overnight. The reaction was allowed to cool to room temperature and the solvent removed in vacuo. The yellow solid obtained was dissolved in a minimum amount of water and extracted with EtOAc (4×50 mL). Organic layers were combined, washed with Na$_2$S$_2$O$_3$ (10% solution, 2×50 mL), water (50 mL) and brine (50 mL). The organic layer was dried over Na$_2$SO$_4$, filtered and concentrated in vacuo to yield 1.68 g (99%) 2,3-dihydroxybenzoic acid as a white solid. $^1$H NMR (CD$_3$OD): 7.34 (d, J =8.0 Hz, 1H), 6.99 (d, J=8.0 Hz, 1H), 6.72 (t, J=8.0 Hz, 1H).

Step 2

Diphenylphosphorylazide (336 µL, 1.56 mmol, 1.2 eq) was added to 2,3-dihydroxybenzoic acid (200 mg, 1.30 mmol) in pyridine (10 mL) and heated at 75° C. for 30 h. Reaction mixture was allowed to cool to room temperature and the reaction was quenched with water. Pyridine was removed in vacuo. The residue was partitioned between EtOAc (20 mL) and saturated aqueous NaHCO$_3$ (20 mL). The aqueous layer was extracted with EtOAc (3×20 mL). The organic layers were combined, washed with brine, dried over Na$_2$SO$_4$, filtered and concentrated in vacuo to yield a thick yellowish oil. The desired product was purified by Biotage flash chromatography (cartridge 40S, SiO$_2$) using 0 to 50% EtOAc/hexane to yield 104 mg (53%) as a white powder. $^1$H NMR (CD$_3$OD) 6.96 (dd, J=7.8, 8.4 Hz, 1H), 6.59 (d, J=8.4 Hz, 1H), 6.56 (d, J=7.8 Hz, 1H).

Step 3

7-Hydroxy-3H-benzooxazol-2-one (300 mg, 1.98 mmol), 5-bromoveratraldehyde (486 mg, 1.98 mmol) and malononitrile (131 mg, 1.98 mmol) were dissolved in ethanol (12 mL). Piperidine (390 µL, 3.96 mmol) was added and the reaction was stirred at room temperature overnight. The precipitate was filtered and dried to yield 339 mg (38%) of the desired 2-amino-4-(3-bromo-4,5-dimethoxyphenyl)-3-cyano-8-oxo-4H-oxazolo[4,5-h]chromene as a light yellow powder. $^1$H NMR (DMSO-d$_6$): 11.79 (s, 1H), 7.21 (brs, 2H), 6.98 (s, 1H), 6.91 (s, 1H), 6.85-6.79 (m, 2H), 4.79 (s, 1H), 3.78 (s, 3H), 3.68 (s, 3H).

Step 4

2-amino-4-(3-bromo-4,5-dimethoxyphenyl)-3-cyano-8-oxo-4H-oxazolo[4,5-h]chromene (335 mg, 0.75 mmol) and cesium carbonate (270 mg, 0.83 mmol) were diluted in dry acetone (10 mL). Methyl iodide (2M solution in tert-butyl methyl ether, 415 µL, 0.83 mmol) was added and the reaction was stirred at room temperature overnight. Solvent was removed in vacuo and the residue was partitioned between water (20 mL) and EtOAc (60 mL). The aqueous layer was extracted with EtOAc (2×50 mL). The organic layers were combined, dried over Na$_2$SO$_4$, filtered and concentrated to a yellow solid. The product was isolated by flash chromatography using a 25S SiO$_2$ system by Biotage, Inc., Charlottesville, Va., using 0 to 1% methanol in dichloromethane to yield 292 mg (85%) 2-amino-4-(3-bromo-4,5-dimethoxyphenyl)-3-cyano-7-methyl-8-oxo-4H-oxazolo[4,5-h]chromene as a light yellow solid. $^1$H NMR (Acetone-d$_6$) 7.04-6.93 (m, 4H), 6.49 (brs, 2H), 4.83 (s, 1H), 3.86 (s, 3H), 3.76 (s, 3H), 3.39 (s, 3H).

Step 5

At 0° C., tert-butylnitrite (62 µL, 0.52 mmol) was added to 2-amino-4-(3-bromo-4,5-dimethoxyphenyl)-3-cyano-7-methyl-8-oxo-4H-oxazolo[4,5-h]chromene (20 mg, 0.044 mmol) in dry THF (1 mL) and was stirred at this temperature for 2 h. Sodium borohydride (19.8 mg, 0.52 mmol) was added and the reaction was stirred at 0° C. for 3 h. Reaction was quenched with NH$_4$Cl saturated aqueous solution (1 mL) and the mixture was partitioned between water (2 mL) and EtOAc (5 mL). The aqueous layer was extracted with EtOAc (2×5 mL). The organic layers were combined, washed with saturated NaHCO$_3$ (5 mL), brine (5 mL), dried over Na$_2$SO$_4$, filtered and concentrated to a yellow oil. The product was isolated by flash chromatography using a 12S SiO$_2$ system by Biotage, Inc., Charlottesville, Va., using 1 to 2% EtOAc in dichloromethane to yield 10 mg (85%) of 4-(3-bromo-4,5-dimethoxyphenyl)-3-cyano-7-methyl-8-oxo-4H-oxazolo[4,5-h]chromene as a light yellow solid. $^1$H NMR (Acetone-d$_6$) 7.80 (d, J=1.2 Hz, 1H), 7.13-7.11 (m, 2H), 6.99-6.96 (m, 2H), 5.00 (s, 1H), 3.87 (s, 3H), 3.78 (s, 3H), 3.39 (s, 3H).

EXAMPLE 8

3-Cyano-7-methoxy-4-(3,4,5-trimethoxyphenyl)-4H-chromene

2-Amino-3-cyano-7-methoxy-4-(3,4,5-trimethoxy-phenyl)-4-chromene (45 mg, 0.12 mmol) was dissolved into THF (2 mL) and cooled to −30° C., then tert-butylnitrite (0.15 mL, 1.44 mmol, 12 eq.) was added. The mixture was stirred for 2 h during which the solution was warmed to 0° C. The solution became clear and was cooled to −10° C., then sodium borohydride (54 mg, 1.44 mmol, 12 eq) was added. Reaction mixture was stirred at room temperature for 1 h. Then it was quenched with NH$_4$Cl saturated solution (10 mL) and diluted with EtOAc (10 mL). The organic phase was washed with saturated NH$_4$Cl (10 mL), saturated NaHCO$_3$ (10 mL), water (10 mL) and brine (10 mL), dried over Na$_2$SO$_4$ and concentrated. Purification with bond elute silica gel cartridge using 20% EtOAc/hexane yielded 42 mg (50%) as a white solid. $^1$H NMR (CDCl$_3$) 7.28 (d, J=1.2 Hz, 1H), 6.87 (dd, J=0.4, 8.6 Hz 1H), 6.64 (dd, J=2.6, 8.6 Hz, 1H,), 6.56 (d, J=2.6 Hz, 1H), 6.38 (s, 2H), 4.60 (s, 1H), 3.82 (s, 3H), 3.81 (s, 6H), 3.79 (s, 3H).

EXAMPLE 9

7-Dimethylamino-4-(3,4,5-trimethoxyphenyl)-2H-chromene

Step 1

Sodium hydride (57 mg, 1.7 mmol) was added to a mixture of acrylonitrile (4.07 g, 77 mmol ) and dimethylaminophenol (5 g, 37 mmol). The reaction mixture was cooled to 0° C. and treated with glacial acetic acid (0.11 mL). The excess of acrylonitrile was removed by vacuo and the residue was dissolved in ether (10 mL). A purple precipitate was formed. The solution was filtered, concentrated and dried on a vaccum pump overnight. Purification by Biotage flash chromatography using 30% EtOAc/hexane yielded 5.6 g (80%) of the desired compound as a white solid. $^1$H NMR (CDCl$_3$) 7.20-7.16 (m, 1H), 6.4-6.30 (m, 3H), 4.23 (t, J=6.5 Hz, 2H), 2.97 (s, 6H), 2.84 (t, J=6.5 Hz, 2H).

Step 2

3-(3-Dimethylamino-phenoxy)-propionitrile (4.85 g, 25.5 mmol) was dissolved into concentrated hydrochloric acid (35 mL). The reaction mixture was heated to 85° C. and then refluxed for 4 h at a temperature of 109° C. The reaction mixture was allowed to cool to room temperature overnight. Solvent was evaporated under high vacuum to yield a pink solid. The solid was washed with isopropanol, then it was dissolved into water (100 mL) and pH was adjusted to 3-5 with NaHCO$_3$ saturated solution. The product precipitated. Solid was collected and dried on a vaccum pump overnight. (1.55 g, 29%): $^1$H NMR (CDCl$_3$): 10.08 (brs, 1H), 7.20-7.16 (m, 1H), 6.45-6.35 (2m, 3H), 4.28 (t, J=6.4 Hz, 2H), 2.96 (s, 6H), 2.87 (t, J=6.4 Hz, 2H).

Step 3

Polyphosphoric acid (15 mL) was added to 3-(3-Dimethylamino-phenoxy)-propionic acid (1.55 g, 7.4 mmol). The reaction mixture was stirred at 60° C. to incorporate the solid into the viscous polyphosphoric acid. The reaction was heated to 77° C. for 5 h then the solution was allowed to cool overnight. Reaction mixture was heated to 60° C. and poured into water (750 mL). The solution was neutralized to pH 7 with saturated NaHCO$_3$ solution. The solution was extracted with EtOAc (3×200 mL) Combined extracts were washed with brine (300 mL), dried over MgSO$_4$, and concentrated to yield a green solid. Purification by flash chromatography on a system by Biotage, Inc., Charlottesville, Va., using 50% EtOAc/hexane yielded 816 mg (57%) as a green solid. $^1$H NMR (CDCl$_3$) 7.77 (d, J=8.9 Hz, 1H), 6.36 (dd, J=2.5, 8.9 Hz, 1H), 6.06 (d, J=2.3 Hz, 1H), 4.48-4.45 (m, 2H), 3.03 (s, 6H), 2.72-2.68 (m, 2H).

Step 4

To a solution of trimethoxyiodobenzene (159 mg, 0.54 mmol) in THF (2.5 mL) at −78° C. was added n-butyl lithium solution (1.6 M in hexane, 0.34 mL). The reaction mixture was stirred 10 min, then a solution of 7-dimethylamino-chroman-4-one (103 mg, 0.54 mmol) in THF (2.5 mL) was added and stirring continued at −78° C. for 1 h followed by room temperature overnight. The reaction became orange, NH$_4$Cl saturated solution (1 mL) was added and the mixture was diluted with EtOAc (25 mL). The organic layer was washed with water (25 mL), brine (25 mL), dried over magnesium sulfate and concentrated to yield a yellow oil. The residue was dissolved in ethanol (6 mL) and treated with concentrated hydrochloric acid (2 mL). The mixture was heated to reflux for 90 min, allowed to cool, diluted with EtOAc (25 mL) and washed with water (2×25 mL), 10% sodium thiosulfate (25 mL) and water (25 mL). The organic layer was dried over MgSO$_4$ and concentrated to yield a yellow oil. Purification by Biotage flash chromatography using 50% EtOAc/hexane gave a mixture of compounds. Another purification was done using 20% EtOAc/hexane and yielded 30 mg (16%) as a green oil. $^1$H NMR (CDCl$_3$): 6.97 (d, J=8.5 Hz, 1H), 6.59 (s, 2H), 6.35-6.25 (2m, 2H), 5.61 (s, 1H), 4.82 (d, J=4.0 Hz, 2H), 3.91 (s, 3H), 3.87 (s, 3H), 2.99 (s, 3H).

EXAMPLE 10

3-Chloro-7-dimethylamino-4-(3,4,5-trimethoxyphenyl)-2H-chromene

Step 1

Cupric chloride (85 mg, 0.634 mmol) and lithium chloride (14 mg, 0.317 mmol) were stirred at 80° C. in 0.5 mL of DMF until complete dissolution (10 min). 7-Dimethylamino-chroman-4-one (50 mg, 0.264 mmol) was added and stirring was maintained at 80° C. for 1 h. The reaction mixture was allowed to cool to room temperature and diluted with 15 mL of ether and washed with 10 mL of water. The etheral phase was dried over sodium sulfate and concentrated. Purification by flash chromatography using 15% EtOAc/hexane yielded 31 mg (52%0 of the desired compound as a pale yellow solid. $^1$H NMR (CDCl$_3$): 7.80 (d, J=9.1 Hz, 1H,), 6.42 (dd, J=2.3, 9.1 Hz, 1H), 6.09 (d, J=2.3 Hz, 1H), 4.62-4.57 (m, 1H), 4.51-4.44 (m, 2H), 3.07 (s, 6H).

Step 2

Iodotrimethoxybenzene (40 mg, 0.133 mmol) was dissolved into 1 mL of dry THF and cooled to −78° C. The butyl lithium solution 1.16 M (126 μL, 0.146 mmol, 1.1 eq.) was added dropwise and the mixture was stirred at −78° C. for 15 min. 3-Chloro-7-dimethylamino-chroman-4-one (30 mg, 0.133 mmol) in 1 mL of dry THF was added and the mixture was allowed to warm to room temperature. After 3 h, the mixture was quenched with a saturated aqueous solution of NH$_4$Cl (10 mL) and extracted with EtOAc (2×10 mL). Combined organic extracts were dried with Na$_2$SO$_4$ and concentrated. The residue was diluted in a mixture of 2 mL of ethanol and 0.75 mL of concentrated hydrochloric acid, and stirred overnight at room temperature. A saturated solution of sodium bicarbonate was added until neutralization and the resulting solution was extracted with EtOAc (2×25 mL).

The organic phase was dried over Na$_2$SO$_4$ and concentrated. The crude compound was purified by flash chromatography using 15% EtOAc/hexane to yield 18 mg (35%) of the desired compound as a pale yellow solid. $^1$H NMR (CDCl$_3$): 6.65 (d, J=8.6 Hz, 1H), 6.50 (s, 2H), 6.29-6.22 (m, 2H), 4.88 (s, 2H), 3.92 (s, 3H), 3.85 (s, 6H), 2.96 (s, 6H).

EXAMPLE 11

3-Cyano-7-methoxy-4-(3,4,5-trimethoxyphenyl)-chroman

3-Cyano-7-methoxy-4-(3,4,5-trimethoxy-phenyl)-4H-chromene (25 mg, 0.07 mmol) was dissolved into EtOAc (1 mL). The solution was purged with nitrogen, and a catalytic amount of Pd/C 10% was added. The reaction was put under H$_2$ pressure at 60 psi for 5 h. The solution was flushed with nitrogen, filtered on a Celite pad, and the pad was washed with EtOAc (5 mL). The solution was concentrated. Purification with bond elute silica gel using 20% EtOAc/hexane yielded 24 mg (72%) as a white solid. $^1$H NMR (CDCl$_3$): 6.83 (d, J=8.3 Hz, 1H), 6.51 (d, J=2.6 Hz, 1H), 6.48 (dd, J=2.5, 5.1 Hz, 1H), 6.45 (s, 2H), 4.38-4.33 (m, 3H), 3.86 (s, 3H), 3.80 (s, 9H), 3.40-3.37 (m, 1H).

EXAMPLE 12

4-(3-Bromo-4,5-dimethoxyphenyl)-3-cyano-2-hydroxy-pyrrolo[2,3-h]chroman a) 3-(3-Bromo-4,5-dimethoxyphenyl)-2-dimethoxymethyl-acrylonitrile. To a solution of 3-bromo-4,5-dimethoxybenzaldehyde (451 mg, 1.84 mmol) and 3,3-dimethoxypropionitrile (307 mg, 2.667 mmol) in methanol (10 mL) at approximately 0° C. was added approximately 21% sodium ethoxide solution in ethanol (1 mL). The brown solution was stirred at room temperature for approximately 23 h. The reaction mixture was transferred to a sealed tube and heated in an oil bath at approximately 80° C. for approximately 34 h. The solvent was evaporated under vacuum. The residue was dissolved in EtOAc (30 mL), washed with water (10 mL), dried over $MgSO_4$, and evaporated to yield a brown oil. The crude product was purified by column chromatography (silica gel, EtOAc:hexanes, 1:9) to yield 69 mg (22%) of the product. $^1H$ NMR ($CDCl_3$): 7.65 (d, J=2.1 Hz, 1H), 7.39 (dd, J=0.6, 2.4 Hz, 1H), 7.20 (m, 1H), 5.03 (d, J=1.2 Hz, 1H), 3.93 (s, 3H), 3.91 (s, 3H), 3.42 (s, 3H).

b) 3-(3-Bromo-4,5-dimethoxy-phenyl)-2-formyl-acrylonitrile. 3-(3-bromo-4,5-dimethoxy-phenyl)-2-dimethoxymethyl-acrylonitrile (50 mg, 0.146 mmol) was stirred in approximately 50% HCl solution (1 mL) for approximately 30 min. The suspension was diluted with $H_2O$ (5 mL), extracted with $CH_2Cl_2$ (2×10 mL). The $CH_2Cl_2$ extracts were washed with saturated aqueous $NaHCO_3$ (5 mL) solution, dried over $MgSO_4$, and evaporated to yield 40 mg (92%) as a yellow solid. The crude was used without purification. $^1H$ NMR ($CDCl_3$): 9.57 (s, 1H), 7.88 (d, J=2.4 Hz, 1H), 7.75 (s, 1H), 7.61 (d, J=2.1 Hz, 1H), 4.00 (s, 3H), 3.96 (s, 3H).

c) 4-(3-Bromo-4,5-dimethoxyphenyl)-3-cyano-2-hydroxy-pyrrolo[2,3-h]chroman. To a suspension of the above aldehyde (30 mg, 0.101 mmol) and 4-hydroxyindole (21 mg, 0.158 mmol) in absolute ethanol (10 mL) was added piperidine (0.1 mL). The clear solution was stirred at room temperature overnight. The solvent was evaporated and the residue was purified by column chromatography (silica gel, EtOAc:hexanes, 1:5 to 2:5). The title compound was obtained as an off-white solid (12 mg, 32%): $^1H$ NMR ($CDCl_3$): 8.22 (s, 1H), 7.20-7.16 (m, 1H), 7.04-6.94 (m, 2H), 6.80-6.54 (m, 2H), 5.96-5.62 (m, 1H), 4.64-4.44 (m, 1H), 3.89, 3.88, 3.88 (3s, 3H), 3.82, 3.80, 3.80 (3s, 3H), 3.65-3.54 (m, 1H), 3.40-3.18 (m, 1H).

EXAMPLE 13

3-Cyano-7-methoxy-2-oxo-4-(3,4,5-trimethoxyphenyl)-chroman

2-Amino-3-cyano-7-methoxy-4-(3,4,5-trimethoxyphenyl)-4H-chromene (260 mg, 0.7 mmol) was dissolved into approximately 5 mL of formic acid. The obtained white suspension was stirred approximately 1 h at room temperature until it solubilized. The solvent was evaporated. The residue was dissolved into ethyl acetate (20 mL), washed with sodium bicarbonate saturated solution (2×20 mL), brine (20 mL), dried over sodium sulfate and concentrated to give approximately 210 mg of a mixture of diastereoisomers. $^1H$ NMR ($CDCl_3$): 7.12 (d, J=8.2 Hz, 0.5H), 6.82-6.67 (m, 2.5H), 6.41 (s, 1H), 6.37 (s, 1H), 4.48-4.43 (m, 1H), 4.25-4.02 (m, 1H), 3.86-3.78 (4s, 12H)

EXAMPLE 14

4-(3-Bromo-4,5-dimethoxyphenyl)-3-cyano-2-oxo-pyrrolo[2,3-h]chroman

The title compound was prepared using a procedure similar to that in Example 13. $^1H$ NMR (DMSO-$d_6$): 11.51-11.41 (2s, 1H), 7.44-6.26 (m, 6H, complex mixture), 5.52-4.90 (2m, 2H), 3.77 (s, 3H), 3.75 (s, 3H)

EXAMPLE 15

4-(3-Bromo-4,5-dimethoxyphenyl)-7-dimethylamino-2-hydroxy-chroman a) A mixture of 5-bromoveratraldehyde (100 mg, 0.41 mmol) and (triphenylphosphoranylidene)acetaldehyde (137 mg, 0.45 mmol) in dry benzene (2.5 ml) was refluxed for 9 h and the solvent was removed. The crude product was passed through a short silica gel column (bond-elute) (eluents: 10% ethyl acetate in hexane), giving 3-(3-bromo-4,5-dimethoxyphenyl)-propenal (50 mg, 45%). $^1H$ NMR ($CDCl_3$): 9.68 (d, J=7.6 Hz, 1H), 7.36 (d, J =1.8 Hz, 1H), 7.34 (d, J=15.8 Hz, 1H), 7.03 (d, J=1.9 Hz, 1H), 6.62 (dd, J=7.6, 16.0 Hz, 1H), 3.913 (s, 3H), 3.907 (s, 3H) (the sample contained trace amount of starting material).

b) A mixture of the 3-(3-bromo-4,5-dimethoxy-phenyl)-propenal (200 mg; 0.74 mmol), 3-(dimethylamino)phenol (101 mg, 0.74 mmol) and morpholine (65 µl; 0.75 mmol) in dry methanol (5 ml) was refluxed for 2 h and stirred at room temperature for 16 h. The solvent was removed and the intermediate [4-(3-bromo-4,5-dimethoxy-phenyl)-2-morpholin-4-yl-chroman-7-yl]-dimethyl-amine was obtained (350 mg).

c) The [4-(3-bromo-4,5-dimethoxy-phenyl)-2-morpholin-4-yl-chroman-7-yl]-dimethyl-amine was hydrolyzed to the lactol by heating 160 mg of crude solid in a mixture of acetic acid (2 ml) and water (2.4 ml) at 50° C. for 20 min. The reaction mixture was slowly added to saturated $NaHCO_3$. It was extracted with dichloromethane (100 ml) and washed with brine (10 ml). The extract was dried over sodium sulphate and the solvent was evaporated. The crude product was passed through a bond-elute (hexane:ethyl acetate=9:1 and 4:1), yielding the title compound (110 mg; 80%). $^1H$ NMR ($CD_3OD$): 6.96 and 6.91 (two broad signals, 1H), 6.82 and 6.80 (two broad signals, 1H), 6.58 and 6.51 (d each, J=8.6 Hz, 1H), 6.28-6.34 (m, 1H), 6.23 and 6.22 (d each, J=2.1 Hz, 1H), 5.47 (broad signal) and 5.37 (d, J=8.9 Hz) (1H), 4.11-4.17 (m, 1H), 3.795, 3.793, 3.785 and 3.782 (s each, 6H), 2.871 and 2.868 (s each, 6H), 1.87-2.15 (m, 2H).

EXAMPLE 16

4-(3-Bromo-4,5-dimethoxyphenyl)-7-dimethylamino-2-methoxy-chroman

A mixture of [4-(3-bromo-4,5-dimethoxyphenyl)-2-morpholin-4-yl-chroman-7-yl]-dimethyl-amine (10 mg; 0.021 mmol) and p-toluene sulphonic acid (8 mg) in methanol (1 ml) was stirred overnight at room temperature. The mixture was cooled to 0° C. Acetyl chloride (10 µl) was added and the reaction was stirred at room temperature for 0.5 h. TLC showed formation of product. Another 10 µl of acetyl chloride was added at 0° C., and the mixture was stirred for 0.5 h at room temperature. It was neutralized with saturated sodium bicarbonate and extracted with dichloromethane. The extract was washed with saturated sodium chloride solution, dried and evaporated. The title compound was obtained by passing the crude product through a bond-elute (hexane:ethyl acetate=9:1 as eluent) (yield: 51%). $^1H$ NMR (acetone-$d_6$): 7.00, 6.99, 6.97 and 6.93 (d each, J=1.8 Hz; 2H), 6.54 (t, J=9.6 Hz; 1H), 6.28-6.31 (two doublets overlapped, J=8.5 Hz; fine splitting J=2.2 Hz; 1H), 6.22-6.23 (two doublets, J=3.3 Hz; 1H), 5.18 (t, J=2.5 Hz) and 5.12 (dd, J=2.4, 7.8 Hz) (1H), 4.08-4.15 (m, 1H), 3.87, 3.84, 3.80 and 3.79, (s each, 6H), 3.53 and 3.47 (s each, 3H), 2.91 and 2.90 (s each, 6H), 2.29-2.35 (m) and 1.98-2.19 (m, overlapping with acetone signal) (2H).

EXAMPLE 17

2-Acetoxy-4-(3-bromo-4,5-dimethoxyphenyl)-7-dimethylamino-chroman

To a mixture of 4-(3-bromo-4,5-dimethoxyphenyl)-7-dimethylamino-2-hydroxy-chroman (9 mg, 0.022 mmol), dimethylamino-pyridine (catalytic) and pyridine (0.1 ml) in dichloromethane at 0° C. was added acetic anhydride (0.05 ml). The mixture was stirred overnight at room temperature. To the mixture was added ice and the mixture was extracted with dichloromethane. The extract was washed with 1N HCl, saturated $NaHCO_3$ and saturated sodium chloride solution, dried and the solvent was evaporated. The title compound was obtained upon chromatography of the crude material over a bond-elute (hexane:ethyl acetate=9:1 and 4:1 as eluent) (6.0 mg; 61%). $^1$H NMR ($CD_3OD$): 6.99 (d, J=1.9 Hz), 6.86 (broad signal) and 6.85 (d, J=1.8 Hz) (2H), 6.72 (d, J=8.8 Hz) and 6.54 (d, J=8.5 Hz) (1H), 6.47 (t, J=2.3 Hz) and 6.42 (dd, J=2.2, 9.2 Hz) (1H), 6.35 (overlapping dd, J=2.5, 8.7 Hz) (1H), 6.26 (d, J=2.3 Hz) and 6.22 (d, J=2.5 Hz) (1H), 4.14 (overlapping dd, J=6.0, 11.9 Hz; 1H), 3.76-3.80 (s, 6H), 2.87 and 2.91 (s each, 6H), 2.40-2.45 and 2.11-2.32 (m each; 2H), 2.08 and 1.79 (s each, 3H).

EXAMPLE 18

4-(3-Bromo-4,5-dimethoxyphenyl)-2-hydroxy-7-methyl-pyrrolo[2,3-h]chroman

A mixture of 4-hydroxy-N-methyl indole (11 mg, 0.075 mmol) and 3-(3-bromo-4,5-dimethoxyphenyl)-propenal (20 mg, 0.074 mmol) in methanol (0.6 ml) containing morpholine (7 µl, 0.08 mmol) was held under reflux for 2 h and the mixture was allowed to stir at room temperature overnight. The solvent was evaporated to dryness. The residue was dissolved in acetic acid (0.8 ml) and water was added until the mixture became turbid. It was held at 50° C. for 10 minutes. It was cooled and added slowly to saturated sodium bicarbonate solution. The product was extracted with dichloromethane, washed with saturated sodium chloride solution and dried over sodium sulphate. The solvent was evaporated and the crude product was passed through a bond-elute (hexane:ethyl acetate=9:1 and 8:2 as eluents), giving the title compound (16 mg, 52%). $^1$H NMR (acetone-$d_6$): 7.09 and 7.08 (d each, J=2.9 Hz; 1H), 7.00 and 6.98 (d each, J=1.7 Hz; 1H), 6.95 and 6.93 (d each, J=1.7 Hz; 1H), 6.85 and 6.83 (d each, J=8.6 Hz; 1H), 6.55 and 6.50 (d each, J=8.5 Hz; 1H), 6.42 and 6.41 (d each, J=3.3 Hz; 1H), 6.15 (fine split doublet, J=6.8 Hz) and 6.08 (d, J=4.9 HZ) (1H), 5.67-5.70 and 5.54-5.58 (m each, 1H), 4.34 (overlapping dd, J=5.8, 10.1 Hz; 1H), 3.84, 3.81, 3.78 and 3.75 (s each, 9H), 2.38-2.43 and 2.09-2.25 (m each, 2H).

EXAMPLE 19

4-(3-Bromo-4,5-dimethoxyphenyl)-2-methoxy-7-methyl-pyrrolo[2,3-h]chroman

To a solution of 4-(3-bromo-4,5-dimethoxyphenyl)-2-hydroxy-7-methyl-pyrrolo[2,3-h]chroman (5 mg; 0.012 mmol) in methanol (0.5 ml) at 0° C. was added acetyl chloride (10 µl). The mixture was warmed to room temperature and stirred at this temperature for 3 h. Saturated sodium bicarbonate solution was added and the reaction mixture was extracted with dichloromethane. The extract was washed with saturated sodium chloride solution, dried and evaporated. The crude product was passed through bond-elute (hexane:ethyl acetate=9:1 as eluent), giving the title compound (3 mg; 58%). $^1$H NMR (acetone-$d_6$): 7.14 (d, J=2.7 Hz) and 7.13 (d, J=2.9 Hz) (1H), 6.94-7.02 (m, 2H), 6.89 and 6.88 (d each, J=8.5 Hz, 1H), 6.50-6.57 (m, 2H), 5.32 (t, J=2.6 Hz) and 5.27 (dd, J=2.3, 7.6 Hz) (1H), 4.34 (dd, J=6.6, 9.5 Hz) and 4.27 (dd, J=6.0, 11.3 Hz) (1H), 3.85, 3.82, 3.81, 3.80, 3.79, 3.78 (s each, 9H), 3.59 and 3.50 (s each, 3H), 2.43 (ddd, J=2.3, 6.6, 13.3 Hz) and 2.12-2.30 (m) (2H).

EXAMPLE 20

2-Acetoxy-4-(3-bromo-4,5-dimethoxyphenyl)-7-methyl-pyrrolo[2,3-h]chroman

To a solution of 4-(3-bromo-4,5-dimethoxyphenyl)-2-hydroxy-7-methyl-pyrrolo[2,3-h]chroman (37 mg, 0.089 mmol) in dichloromethane (0.5 ml) at 0° C. was added pyridine (0.010 ml, 0.133 mmol), 4-dimethylaminopyridine (1.0 mg, 0.0082 mmol) and acetic anhydride (0.010 ml, 0.111 mmol) and the resulting solution was stirred at 0° C. for 0.5 h. The solution was then stirred at room temperature for 1.5 h. The reaction mixture was diluted with dichloromethane and the organic solution was extracted with water and a saturated aqueous solution of sodium bicarbonate. The organic layer was dried and concentrated in vacuo. The residue was purified by flash chromatography (20% ethyl acetate/hexane) to give 39 mg (90%) of the title compound. $^1$H NMR ($CD_3CN$): 7.10 (dd, 1H); 7.02 (m, 1H); 6.94-6.84 (m, 2H); 6.72-6.60 (m, 1H); 6.53 (m, 1H); 6.43 (m, 1H); 4.38-4.19 (m, 1H); 3.80-3.74 (m, 9H); 2.56-2.40 (m, 1H); 2.32 (m, 1H); 1.96 (s, 3H).

EXAMPLE 21

4-(3-Bromo-4,5-dimethoxyphenyl)-7-methyl-pyrrolo[2,3-h]chroman-2-one

To a mixture of 4-(3-bromo-4,5-dimethoxyphenyl)-2-hydroxy-7-methyl-pyrrolo[2,3-h]chroman (6 mg; 0.014 mmol), molecular sieves 4A° (20 mg) and 4-methylmorpholin-N-oxide (2 mg; 0.017 mmol ) in dichloromethane (0.5 ml) at 0° C. was added TPAP (0.4 mg). The mixture was stirred at this temperature for 0.5 h and at room temperature for 20 min. It was concentrated and passed through a bond-elute (hexane:ethyl acetate=9:1 and 4:1 as eluents), yielding the title compound (1.2 mg; 20%). $^1$H NMR (acetone-$d_6$): 7.30 (d, J=3.1 Hz; 1H), 7.21 (dd, J=0.8, 8.4 Hz; 1H), 7.03 (d, J=2.0 Hz; 1H), 6.92 (d, J=8.4 Hz; 1H), 6.87 (dd, J=0.6, 2.1 Hz; 1H), 6.55 (dd, J=0.8, 3.1 Hz; 1H), 4.55 (t, J=5.9 Hz; 1H), 3.86, 3.84, 3.77 (s each, 9H), 3.24 (dd, J=6.4, 15.8 Hz; 1H), 3.13 (dd, J=5.9, 15.8 Hz; 1H).

EXAMPLE 22

4-(3-Bromo-4,5-dimethoxyphenyl)-7-methyl-pyrrolo[2,3-h]chroman

To a solution of acetic acid 4-(3-bromo-4,5-dimethoxyphenyl)-7-methyl-pyrrolo[2,3-h]chroman-2-yl ester (12 mg; 0.026 mmol) at 0° C. was added lithium aluminium hydride (2 mg) and the mixture was stirred for 20 min at 0° C. Additional lithium aluminium hydride (8 mg) was added and the reaction was complete in 10 min. Water was added slowly to destroy the excess LAH. The mixture was diluted with ether and dried over sodium sulphate. The solvent was removed and the crude product was passed through a bond-elute (hexane:ethyl acetate=4:1 and 1:1 as eluents) giving the pure di-ol (3 mg).

A mixture of the di-ol, triphenyl phosphine (8.5 mg; 0.032 mmol) and DEAD (3 μl) in THF was stirred at room temperature overnight. The solvent was evaporated down to dryness and passed through a bond-elute (hexane:ethyl acetate=9:1, 4:1 and 1:1 as eluents), yielding the title compound (2.1 mg; 20%). $^1$H NMR (acetone-$d_6$): 7.10 (d, J=2.9 Hz; 1H), 6.94 (ill-resolved d, J=1.8 Hz; 1H), 6.88 (d, J=8.4 Hz; 1H), 6.85 (ill-resolved d, J=2.0 Hz; 1H), 6.62 (d, J=8.4 Hz; 1H), 6.44 (d, J=3.1 Hz; 1H), 4.17-4.28 (m, 3H), 3.82, 3.77 (s each, 9H), 2.31-2.39 (m, 1H), 2.08-2.15 (m, 1H).

EXAMPLE 23

7-Methoxy-2-hydroxy-4-(3,4,5-trimethoxyphenyl)-chroman 3-(3,4,5-Trimethoxyphenyl)-propenal was prepared following the procedure for 3-(3-bromo-4,5-dimethoxyphenyl)-propenal as described in Example 15a using 3,4,5-trimethoxy benzaldehyde. 7-Methoxy-2-hydroxy-4-(3,4,5-trimethoxyphenyl)-chroman was synthesized by the same procedure as Example 18 from 3-(3,4,5-trimethoxyphenyl)-propenal (71 mg; 0.32 mmol) and 3-methoxy phenol (43 mg; 0.35 mmol) using morpholine (30 μl) as a base in methanol (2.5 ml) (14 mg; 13%). $^1$H NMR (acetone-$d_6$): 6.64 (dd, J=1.1, 8.5 Hz) and 6.59 (dd, J=1.0, 8.4 Hz) (1H), 6.54 (one doublet and one singlet overlapped, J=2.7 Hz; 2H), 6.38 (dd, J=2.6, 8.5 Hz; 1H), 6.34 (d overlapping with other small signals, J=2.3 Hz; 1H), 6.13 (d, J=6.8 Hz) and 6.08 (dd, J=1.0, 4.5 Hz) (1H), 5.62-5.65 and 5.47-5.51 (m each, 1H), 4.13-4.21 (overlapping dd, J=6.6, 10.2 Hz; 1H), 3.78, 3.77, 3.73, 3.72 (s each, 12H), 2.31 (ddd, J=2.1, 5.7, 13.1 Hz) and 2.08-2.13 (m, 2H).

EXAMPLE 24

4-(3-Bromo-4,5-dimethoxyphenyl)-2-hydroxy-pyrrolo[2,3-h]chroman

The title compound was prepared following the procedure described in Example 18 from 4-hydroxy indole (10 mg; 0.075 mmol) and 3-(3-bromo-4,5-dimethoxyphenyl)-propenal (20 mg; 0.074) using morpholine (7 μl) as a base in refluxing methanol (0.6 ml) (yield: 33% ). $^1$H NMR (acetone-$d_6$): 10.16 (s, 1H), 7.20 (d, J=3.0 Hz) and 7.19 (d, J=2.5 Hz) (1H), 7.02 (broad d, J=2.0 Hz), 6.97 (broad signal) and 6.93 (d, J=1.8 Hz) (2H), 6.89 and 6.88 (d each, J=8.4 Hz; 1H), 6.49 (d, J=8.8 Hz), 6.47-6.48 (m) and 6.44 (d, J=8.4 Hz) (2H), 6.18 (d, J=6.8 Hz) and 6.10 (d, J=4.5 Hz) (1H), 5.68-5.71 and 5.56-5.62 (m each, 1H), 4.33-4.38 (broad dd, J=5.8, 9.9 Hz; 1H), 3.83, 3.81 and 3.79 (s each, 6H), 2.41 (ddd, J=2.0, 6.1, 12.9 Hz) and 2.08-2.26 (m) (2H).

EXAMPLE 25

2-Hydroxy-7-methyl-4-(3,4,5-trimethoxyphenyl)-pyrrolo[2,3-h]chroman

The title compound was prepared following the procedure described in Example 18 using 4-hydroxy-N-methyl indole (15 mg; 0.1 mmol) and 3-(3,4,5-trimethoxy-phenyl)-propenal (25 mg; 0.11 mmol) with morpholine (10 μl; 0.11 mmol) as a base (yield: 48%). $^1$H NMR (acetone-$d_6$) 6.96 (d, J=2.7 Hz) and 6.94 (d, J=3.1 Hz) (1H), 6.70 (d, J=8.2 Hz) and 6.68 (d, J=7.2 Hz) (1H), 6.45 (d, J=8.6 Hz), 6.43 (s) and 6.40 (d, J=9.0 Hz) (3H), 6.29 and 6.28 (d each, J=3.3 Hz, 1H), 6.01 (d, J=6.8 Hz) and 5.91 (d, J=4.3 Hz) (1H), 5.57-5.60 (m) and 5.42-5.44 (m) (1H), 4.19 (dd, J=6.2, 10.0 Hz; 1H), 3.63, 3.62 and 3.59 (s each, 12 H), 2.23-2.28 (m) and 2.00-2.11 (m) (2H).

EXAMPLE 26

4-(3-Bromo-4,5-dimethoxyphenyl)-2-hydroxy-pyrido[3,4-h]chroman

The title compound was prepared following the procedure in Example 18 from 5-hydroxyisoquinoline (9 mg; 0.062 mmol) and 3-(3-bromo-4,5-dimethoxyphenyl)-propenal (30 mg; 0.11 mmol) using morpholine as a base (10 μl; 0.11 mmol) (yield: 29%). $^1$H NMR (acetone-$d_6$): 9.16 (s, 1H), 8.50 and 8.49 (d each, J=5.7 Hz; 1H), 7.95 (d, J=6.4 Hz) and 7.94 (d, J=5.9 Hz) (1H), 7.51 (d, J=8.4 Hz) and 7.49 (d, J=7.0 Hz) (1H), 6.98-7.07 (m, 3H), 6.65 (d, J=6.6 Hz) and 6.59 (d, J=3.9 Hz) (1H), 5.91-5.93 (m) and 5.74-5.77 (m) (1H), 4.46-4.54 (overlapping dd, J=6.2, 10.5 Hz; 1H), 3.84, 3.81 and 3.80 (s each, 6H), 2.54 (ddd, J=2.1, 6.4, 13.3 Hz) and 2.19-2.38 (m) (2H).

EXAMPLE 27

N-[4-(3-Bromo-4,5-dimethoxyphenyl)-2-hydroxychroman-7-yl]-acetamide

The title compound was prepared following the procedure as in Example 18 from 3-acetamido phenol (13 mg; 0.086 mmol) and 3-(3-bromo-4,5-dimethoxy-phenyl)-propenal (25 mg; 0.09 mmol) using morpholine (15 μl; 0.17 mmol) as a base in reluxing methanol (1 ml) (7 h) (yield: 26%). $^1$H NMR (acetone-$d_6$): 9.06 (s, 1H), 7.36 and 7.34 (broad s each, 1H), 6.89-7.01 (m, 3H), 6.57-6.62 (overlapping d, J=8.4 Hz; 1H), 6.14 (d, J=6.6 Hz) and 6.11 (d, J=4.1 Hz) (1H), 5.62 (broad s) and 5.48-5.50 (m) (1H), 4.19-4.26 (overlapping dd, J=6.2, 11.1 Hz; 1H), 3.85, 3.83 and 3.79 (s each, 6H); 2.34 (broad dd, J=5.9, 12.9 Hz) and 2.09-2.18 (m) (2H), 2.04 (s overlapping with acetone-signal).

EXAMPLE 28

4-(3-Bromo-4,5-dimethoxyphenyl)-2-hydroxy-pyrido[3,2-h]chroman

The title compound was prepared following the procedure as in Example 18 from 3-(3-bromo-4,5-dimethoxyphenyl)-propenal (25 mg; 0.09 mmol) and 8-hydroxyquinoline (9 mg; 0.06 mmol) using morpholine (10 μl; 0.11 mmol) as base (yield: 34%). $^1$H NMR (acetone-$d_6$): 8.85 (overlapping dd, J=1.8, 4.3 Hz; 1H), 8.20 (overlapping dd, J=1.8, 8.4 Hz; 1H), 7.47 (dd, J =4.1, 8.2 Hz, 1H), 7.34 (d, J=8.4 Hz) and 7.32 (d, J=8.4 Hz) (1H), 7.08 (d, J=2.1 Hz), 7.06 (d, J=2.1 Hz) and 7.05 (d, J=2.0 Hz) (2H), 6.98 (d, J=8.8 Hz) and 6.95 (d, J=8.8 Hz) (1H), 5.91 (t, J=2.7 Hz) and 5.70-5.72 (m) (1H), 4.50 (overlapping dd, J=6.3, 10.7 Hz; 1H), 3.85, 3.82, 3.81 and 3.80 (s each, 6H), 2.50-2.56 (m) and 2.20-2.37 (m) (2H).

EXAMPLE 29

4-(3-Bromo-4,5-dimethoxyphenyl)-7,9-dihydro-2-hydroxy-8-oxo-imidazolo[4,5-h]chroman a) A mixture of 2,3-diamino-phenol (50 mg; 0.4 mmol) and 1,1'-carbonyl-diimidazole (65 mg; 0.4 mmol) in THF (5 ml) was stirred overnight. The crude product was purified by chromatography and by washed with water, to give pure 4-hydroxy-1,3-dihydro-benzoimidazole-2-one (32 mg; 53%). $^1$H NMR (DMSO-$d_6$): 10.42 and 10.31 (s each, 2H), 9.46 (s, 1H), 6.70 (t, J=8.0 Hz), 6.41 (dd, J=0.8, 8.2 Hz; 1H), 6.40 (d, J=8.0 Hz).

b) The title compound was prepared following the procedure in Example 18 from 3-(3-bromo-4,5-dimethoxyphenyl)-propenal (25 mg; 0.09 mmol) and 4-hydroxy-1,3-dihydro-benzoimidazole-2-one (17 mg; 0.11 mmol) with morpholine (16 μl; 0.18 mmol) as base (refluxed 3.5 hrs.) (yield: 17%).

$^1$H NMR (acetone-$d_6$): 9.66, 9.61 and 9.57 (s each, 2H), 7.03, 7.01, 6.99 and 6.95 (d each, J=2.0 Hz; 2H), 6.52 and 6.51 (d each, J=8.0 Hz; 1H), 6.30-6.38 (m, 2H), 5.72-5.74 (m) and 5.55-5.63 (m) (1H), 4.32 (broad dd, J=6.6, 9.8 Hz; 1H), 3.85, 3.83, 3.80 and 3.79 (s each, 6H), 2.38 (ddd, J=2.1, 5.9, 13.1 Hz) and 2.10-2.21 (m) (2H).

EXAMPLE 30

4-(3-Bromo-4,5-dimethoxyphenyl)-2-hydroxy-pyrrolo[3,2-h]chroman

The title compound was prepared following the procedure as in Example 18 from 7-hydroxy-indole (0.200 g, 1.50 mmol) and 3-(3-bromo-4,5-dimethoxyphenyl)-propenal (0.416 g, 1.50 mmol) using morpholine (0.143 mL, 1.65 mmol) as a base in refluxing methanol (7.5 mL) (yield: 20%). $^1$H NMR (CDCl$_3$): 10.22 and 10.16 (s each, 1H); 7.27-7.24 (m, 1H); 7.03-6.94 (m, 3H); 6.42-6.36 (m, 2H); 6.21 (d, J=7.6 Hz) and 6.16 (dd, J=5.0, 1.0 Hz) (1H); 5.74-5.71 and 5.61-5.56 (m each, 1H); 4.42-4.36 (m, 1H); 3.83 (s, 3H); 3.79 (s, 3H); 2.85-2.48 and 2.28-2.09 (m each, 2H).

The following compounds were prepared according to the procedures described above.

EXAMPLE 31

7-Methoxy-4-(3,4,5-trimethoxyphenyl)-chroman-2-one $^1$H NMR (CDCl$_3$): 6.92 (d, 1H); 6.71-6.63 (m, 2H); 6.34 (s, 2H); 4.22 (t, 1H); 3.83 (s, 3H); 3.81 (s, 3H); 3.80 (s, 6H); 3.02 (m, 2H).

EXAMPLE 32

4-(3-Hydroxy-4-methoxyphenyl)-6,7,8-trimethoxy-chroman-2-one $^1$H NMR (CDCl$_3$): 6.81 (d, 1H); 6.72 (s, 1H); 6.60 (d, 1H); 6.25 (s, 1H); 5.88-5.40 (m, 1H); 4.17 (m, 1H); 3.98 (s, 3H); 3.90 (s, 3H); 3.87 (s, 3H); 3.70 (s, 3H); 2.95 (m, 2H).

EXAMPLE 33

Identification of 4-(3-bromo-4,5-dimethoxyphenyl)-3-cyano-4H-indolo[4,5-b]pyran and Analogs as Caspase Cascade Activators and Inducers of Apoptosis in Solid Tumor Cells Human breast cancer cell lines T-47D and ZR-75-1 were grown according to media component mixtures designated by American Type Culture Collection +10% FCS (Invitrogen Corporation), in a 5% CO$_2$–95% humidity incubator at 37° C. T-47D and ZR-75-1 cells were maintained at a cell density between 30 and 80% confluency at a cell density of 0.1 to 0.6×10$^6$ cells/mL. Cells were harvested at 600×g and resuspended at 0.65×10$^6$ cells/mL into appropriate media +10% FCS. An aliquot of 45 µL of cells was added to a well of a 96-well microtiter plate containing 5 µL of a 10% DMSO in RPMI-1640 media solution containing 0.16 to 10 µM of 4-(3-bromo-4,5-dimethoxyphenyl)-3-cyano-4H-indolo[4,5-b]pyran (Example 1) or other test compound (0.016 to 1 µM final). An aliquot of 45 µL of cells was added to a well of a 96-well microtiter plate containing 5 µL of a 10% DMSO in RPMI-1640 media solution without test compound as the control sample. The samples were mixed by agitation and then incubated at 37° C. for 24 h in a 5% CO$_2$-95% humidity incubator. After incubation, the samples were removed from the incubator and 50 µL of a solution containing 20 µM of N-(Ac-DEVD)-N'-ethoxycarbonyl-R110 (SEQ ID No.:1) fluorogenic substrate (Cytovia, Inc.; U.S. Pat. No. 6,335,429), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model 1420 Wallac Instruments), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for 4-(3-bromo-4,5-dimethoxyphenyl)-3-cyano-4H-indolo[4,5-b]pyran or other test compound to that of control samples. The EC$_{50}$ (nM) was determined by a sigmoidal dose-response calculation (Prism 2.0, GraphPad Software Inc.). The caspase activity (Ratio) and potency (EC$_{50}$) are summarized in Table I:

TABLE I

| | | Caspase Activity and Potency | | | |
| | | T-47D | | ZR-75-1 | |
| Example | Compound | Ratio | EC$_{50}$ (nM) | Ratio | EC$_{50}$ (nM) |
| --- | --- | --- | --- | --- | --- |
| 1 | (structure) | 7.3 | 8.1 | 36 | 32 |

TABLE I-continued

Caspase Activity and Potency

| | | T-47D | | ZR-75-1 | |
|---|---|---|---|---|---|
| Example | Compound | Ratio | EC$_{50}$ (nM) | Ratio | EC$_{50}$ (nM) |
| 2 | | 5.5 | 6.4 | 37 | 30 |
| 3 | | 5.1 | 7.2 | 7 | 3 |
| 4 | | 5.9 | 2.7 | 5.6 | 2.2 |
| 5 | | 3.6 | 2.4 | 27 | 18 |

TABLE I-continued

Caspase Activity and Potency

| Example | Compound | T-47D Ratio | T-47D EC$_{50}$ (nM) | ZR-75-1 Ratio | ZR-75-1 EC$_{50}$ (nM) |
|---|---|---|---|---|---|
| 6 | | In-active | 4.4 | In-active | 2943 |
| 7 | | 6.7 | 9.3 | 25 | 14 |
| 8 | | 6.7 | 7.7 | 356 | 210 |
| 9 | | 7.8 | 7.9 | 391 | 177 |

TABLE I-continued

Caspase Activity and Potency

| Example | Compound | T-47D Ratio | EC$_{50}$ (nM) | ZR-75-1 Ratio | EC$_{50}$ (nM) |
|---|---|---|---|---|---|
| 10 | (structure) | 8.2 | 7.5 | 490 | 280 |
| 11 | (structure) | 9.6 | 8.3 | 193 | 101 |
| 12 | (structure) | 5.3 | 6.4 | 74 | 53 |
| 13 | (structure) | 4.3 | 5.1 | 203 | 67 |

TABLE I-continued

Caspase Activity and Potency

| Example | Compound | T-47D Ratio | T-47D EC$_{50}$ (nM) | ZR-75-1 Ratio | ZR-75-1 EC$_{50}$ (nM) |
|---|---|---|---|---|---|
| 14 | | 4.8 | 7.6 | 389 | 278 |
| 15 | | 14.6 | 11.4 | 20 | 15 |
| 16 | | 6.8 | 8.3 | 435 | 275 |
| 17 | | 5.2 | 7.2 | 55 | 29 |

TABLE I-continued

Caspase Activity and Potency

| Example | Compound | T-47D Ratio | T-47D EC$_{50}$ (nM) | ZR-75-1 Ratio | ZR-75-1 EC$_{50}$ (nM) |
|---|---|---|---|---|---|
| 18 | | 6.0 | 7.6 | 13.8 | 7.8 |
| 19 | | 4.5 | 6.6 | 52 | 48 |
| 20 | | 4.7 | 7.2 | 5 | 3 |
| 21 | | 6.2 | 5.9 | 285 | 127 |

TABLE I-continued

Caspase Activity and Potency

| | | T-47D | | ZR-75-1 | |
|---|---|---|---|---|---|
| Example | Compound | Ratio | $EC_{50}$ (nM) | Ratio | $EC_{50}$ (nM) |
| 22 | | 6.5 | 6.9 | 58 | 48 |
| 23 | | 6.0 | 6.6 | 48 | 23 |
| 24 | | 2.5 | 2.6 | 100 | 55 |
| 25 | | 10.1 | 7.4 | 7 | 4 |

TABLE I-continued

Caspase Activity and Potency

| Example | Compound | T-47D Ratio | T-47D EC$_{50}$ (nM) | ZR-75-1 Ratio | ZR-75-1 EC$_{50}$ (nM) |
|---|---|---|---|---|---|
| 26 | | 1.1 | 1.8 | >1000 | >1000 |
| 27 | | 1.3 | 5.5 | >1000 | 548 |
| 28 | | 6.5 | 4.5 | 560 | 344 |
| 29 | | 6.0 | 5.0 | 534 | 360 |

TABLE I-continued

Caspase Activity and Potency

| Example | Compound | T-47D Ratio | T-47D EC$_{50}$ (nM) | ZR-75-1 Ratio | ZR-75-1 EC$_{50}$ (nM) |
|---|---|---|---|---|---|
| 30 | | 6.8 | 5.0 | 652 | 379 |
| 31 | | 1.3 | 2.3 | >10000 | 573 |
| 32 | | 4.4 | 4.9 | 3571 | 3081 |
| | | | | >10000 | >10000 |

TABLE I-continued
Caspase Activity and Potency
| | | T-47D | | ZR-75-1 | |
|---|---|---|---|---|---|
| Example | Compound | Ratio | EC$_{50}$ (nM) | Ratio | EC$_{50}$ (nM) |
| | 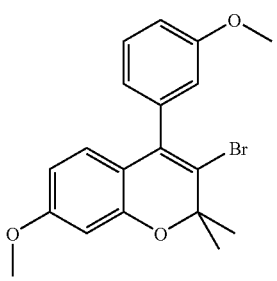 | | | >10000 | >10000 |
| | 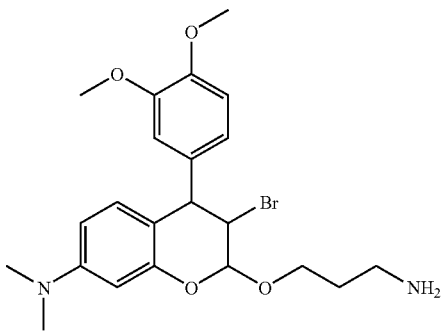 | | | >10000 | >10000 |
| | 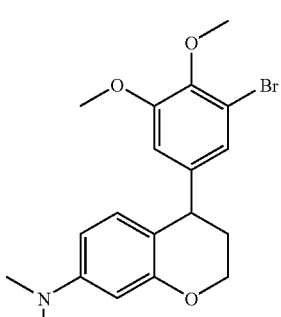 | | | >10000 | >10000 |
| | 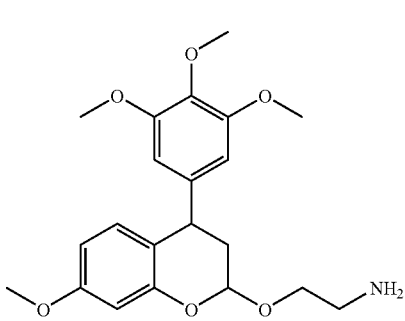 | | | >1000 | >1000 |

TABLE I-continued

Caspase Activity and Potency

| Example | Compound | T-47D Ratio | T-47D EC$_{50}$ (nM) | ZR-75-1 Ratio | ZR-75-1 EC$_{50}$ (nM) |
|---|---|---|---|---|---|
| | [3,5-dichlorophenyl-substituted pyrano-isoquinoline with OH] | | | >1000 | >1000 |
| | [4-methoxyphenyl-substituted 5,6,7-trimethoxy chromen-2-one] | | | >10000 | >10000 |
| | [3,5-dichlorophenyl-substituted pyrano-indole with OH] | | | >1000 | >1000 |
| | [3,4-dimethoxyphenyl-substituted 5,6,7-trimethoxy chromen-2-one] | | | >1000 | >1000 |

TABLE I-continued

Caspase Activity and Potency

| | | T-47D | | ZR-75-1 | |
|---|---|---|---|---|---|
| Example | Compound | Ratio | EC$_{50}$ (nM) | Ratio | EC$_{50}$ (nM) |
| | [4-(3-bromo-4,5-dimethoxyphenyl)-7-amino-2-methoxychroman structure] | | | >1000 | >1000 |
| | [4-(3,5-dichlorophenyl)-7-amino-2-methoxychroman structure] | 1.2 | 1.7 | >10000 | >10000 |
| | [4-(4-methoxyphenyl)-6,7,8-trimethoxychromen-2-one structure] | 5.7 | 8.6 | 5691 | 2653 |
| | [4-(3,5-dichlorophenyl)-7-acetamido-2-hydroxychroman structure] | | | >10000 | >10000 |

Thus, 4-(3-bromo-4,5-dimethoxyphenyl)-3-cyano-4H-indolo[4,5-b]pyran (Example 1) and analogs are identified as potent caspase cascade activators and inducers of apoptosis in solid tumor cells.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A composition comprising a pharmaceutically acceptable carrier and a compound of Formula I:

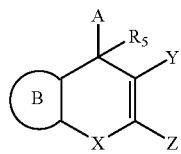

(I)

or pharmaceutically acceptable salts or prodrugs thereof, wherein:
X is O;
Y is CN;
Z is H;
$R_5$ is hydrogen or $C_{1-10}$ alkyl;
A is optionally substituted and is phenyl or pyridyl; and
B is an optionally substituted benzo, indolo, benzimidazolo, benzimidazol-2-one, benzoxazolo, benzoxazol-2-one, benzothienyl, benzofuranyl, quinoxalino or quinoxalin-2-one.

2. The composition of claim 1, wherein said compound is selected from the group consisting of:
  4-(3-Bromo-4,5-dimethoxyphenyl)-3-cyano-7-dimethylamino-4H-chromene;
  4-(3-Bromo-4,5-dimethoxyphenyl)-3-cyano-7-ethylamino-4H-chromene;
  4-(3-Bromo-4,5-dimethoxyphenyl)-3-cyano-7-methoxy-4H-chromeme;
  3-Cyano-4-(5-methyl-3-pyridyl)-4H-indolo[4,5-b]pyran;
  4-(5-Bromo-3-pyridyl)-3-cyano-4H-indolo[4,5-b]pyran;
  4-(3-Bromo-4,5-dimethoxyphenyl)-3-cyano-4H-indolo[4,5-b]pyran;
  4-(3-Bromo-4,5-dimethoxyphenyl)-3-cyano-7-methyl-4H-indolo[4,5-b]pyran;
  4-(3-Bromo-4-hydroxy-5-methoxyphenyl)-3-cyano-7-methyl-4H-indolo[4,5-b]pyran;
  4-(3-Bromo-4,5-dimethoxyphenyl)-3-cyano-7-ethyl-4H-indolo[4,5-b]pyran;
  3-Cyano-7-methyl-4-(5-methyl-3-pyridyl)-4H-indolo[4,5-b]pyran;
  4-(5-Bromo-3-pyridyl)-3-cyano-7-methyl-4H-indolo[4,5-b]pyran;
  3-Cyano-7-methyl-4-(5-methoxy-3-pyridyl)-4H-indolo[4,5-b]pyran;
  4-(3-Bromo-4,5-dimethoxyphenyl)-3-cyano-4H-indolo[7,6-b]pyran;
  3-Cyano-7-methyl-4-(3,4,5-trimethoxyphenyl)-4H-indolo[7,6-b]pyran;
  4-(3-Bromo-4,5-dimethoxyphenyl)-3-cyano-4H-imidazo[4,5-h]chromene;
  4-(3-Bromo-4,5-dimethoxyphenyl)-3-cyano-7-methyl-4H-imidazo[4,5-h]chromene;
  4-(3-Bromo-4,5-dimethoxyphenyl)-3-cyano-7-methyl-8-oxo-4H-oxazolo[4,5-h]chromene;
  4-(3-Bromo-4,5-dimethoxyphenyl)-3-cyano-4H-furo[2,3-h]chromene;
  4-(3-Bromo-4,5-dimethoxyphenyl)-3-cyano-4H-thieno[2,3-h]chromene;
  4-(3-Bromo-4,5-dimethoxyphenyl)-3-cyano-4H-pyrazo[2,3-h]chromene;
  3-Cyano-7-methoxy-4-(3,4,5-trimethoxyphenyl)-4H-chromene;
  3-Cyano-4-phenyl-4H-chromene;and
  pharmaceutically acceptable salts or thereof.

3. A compound of Formula I:

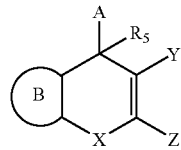

(I)

or pharmaceutically acceptable salts or prodrugs thereof, wherein:
X is O;
Y is CN;
Z is H;
$R_5$ is hydrogen or $C_{1-10}$ alkyl;
A is optionally substituted and is phenyl or pyridyl;

B is an optionally substituted benzo, indolo, benzimidazolo, benzimidazol-2-one, benzoxazolo, benzoxazol-2-one, benzothienyl, benzofuranyl, quinoxalino or ciuinoxalin-2-one.

4. The compound of claim 3, wherein A is phenyl.

5. The compound of claim 3, wherein $R_5$ is hydrogen.

6. A compound of Formula II:

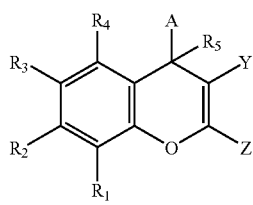

(V)

or pharmaceutically acceptable salts or prodrugs thereof, wherein:

$R_1$-$R_4$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached to form an aryl or partially saturated carbocyclic group, wherein said group is optionally substituted;

$R_5$ is hydrogen or $C_{1-10}$ alkyl;

A is optionally substituted and is phenyl or pyridyl;

Y is CN; and

Z is H.

7. The compound of claim 6, wherein $R_1$ and $R_2$ are taken together with the atoms to which they are attached to form an aryl or partially saturated carbocyclic group, wherein said group is optionally substituted.

8. A compound of Formula II:

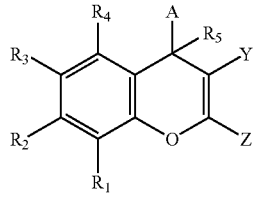

(II)

or pharmaceutically acceptable salts or thereof, wherein:

$R_1$ and $R_2$ are taken together to form a structure selected from the group consisting of —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$, —CH$_2$N(R)CH$_2$CH$_2$—, —N(R)—CH=CH—, —CH=CH—N(R)—, —O—CH=CH—, —CH=CH—O—, —S—CH=CH—, —CH=CH—S—, —CH=CH—CH=CH—, —N=CH—CH=CH—, —CH=N—CH=CH—, —CH=CH—N=CH—, —CH=CH—CH=N—, —N=CH—CH=N—, —N=CH—N(R)—, —N(R)—CH=N—, —N(R)—C(=O)N($R_{15}$)—, —N=CH—O—, —N(R)—C(=O)O—, —O—CH=N—, —O—C(=O)—N(R)—, —N=CH—S—, —N(R)—C(=O)S—, —S—CH=N—, —S—C(=O)—N(R)—; and R and $R_{15}$ are independently hydrogen, $C_{1-10}$ alkyl, haloalkyl, aryl, fused aryl, carbocyclic, alkenyl, alkynyl, arylalkyl, arylalkenyl, arylalkynyl, carbocycloalkyl, hydroxyalkyl or aminoalkyl;

$R_3$ and $R_4$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is phenyl or pyridyl;

Y is CN; and

Z is H.

9. A compound of Formula III:

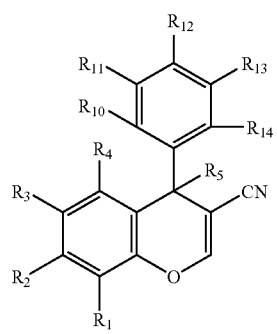

(III)

or pharmaceutically acceptable salts or prodrugs thereof, wherein:

$R_1$-$R_4$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkythiol; or $R_1$ and $R_2$, or $R_2$ and $R_3$, or $R_3$ and $R_4$, taken together with the atoms to which they are attached to form an aryl or partially saturated carbocyclic group, wherein said group is optionally substituted;

$R_5$ is hydrogen or $C_{1-10}$ alkyl; and $R_{10}$-$R_{14}$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached to form an aryl or partially saturated carbocyclic group, wherein said group is optionally substituted.

10. A compound of Formula III:

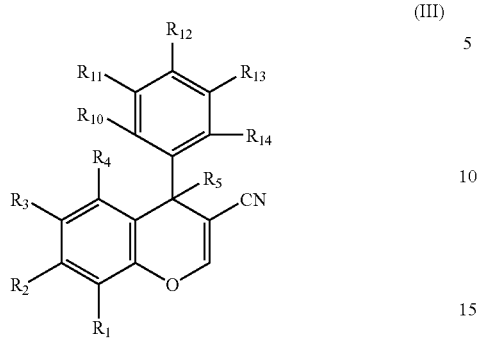

or pharmaceutically acceptable salts or thereof, wherein:
$R_1$-$R_4$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or
$R_1$ and $R_2$, or $R_2$ and $R_3$, or $R_3$ and $R_4$, taken together with the atoms to which they are attached to form an aryl or partially saturated carbocyclic group, wherein said group is optionally substituted;
$R_5$ is hydrogen or $C_{1-10}$ alkyl; and
$R_{10}$-$R_{14}$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or
$R_{10}$ and $R_{11}$, or $R_{11}$ and $R_{12}$, taken together to form a structure selected from the group consisting —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(R)—CH=CH—, —CH=CH—N(R)—, —O—CH=CH—, —CH=CH—O—, —S—CH=CH—, —CH=CH—S—, —CH=CH—CH=CH—, —N=CH—CH=CH—, —CH=N—CH=CH—, —CH=CH—N=CH—, —CH=CH—CH=N—, —N=CH—CH=N—, —N=CH—N(R)—, —N(R)—CH=N—, —N(R)—C(=O)N(R$_{15}$)—, —N=CH—O—, —N(R)—C(=O)O—, —O—CH=N—, —O—C(=O)—N(R)—, —N=CH—S—, —N(R)—C(=O)S—, —S—CH=N—, —S—C(=O)—N(R)—, wherein R and $R_{15}$ are independently hydrogen, $C_{1-10}$ alkyl, haloalkyl, aryl, fused aryl, carbocyclic, alkenyl, alkynyl, arylalkyl, arylalkenyl, arylalkynyl, carbocycloalkyl, hydroxyalkyl or aminoalkyl.

11. The compound of claim 9, wherein $R_1$-$R_2$ are independently hydrogen, halogen, hydroxy, $C_{1-10}$ alkyl, hydroxyalkyl, aminoalkyl, carboxyalkyl, amino, acylamido, acyloxy, alkoxy, methylenedioxy or alkylthiol.

12. The compound of claim 9, wherein $R_5$ is hydrogen.

13. The compound of claim 9, wherein $R_1$ and $R_2$ are taken together with the atoms to which they are attached to form an aryl partially saturated carbocyclic group, wherein said group is optionally substituted.

14. A compound of Formula III:

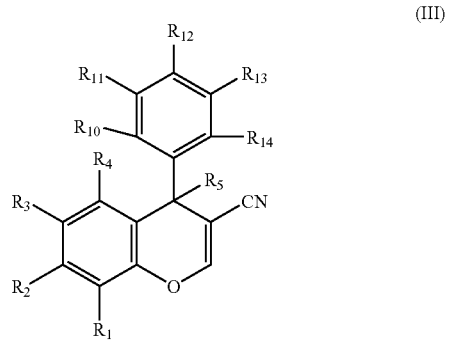

or pharmaceutically acceptable salts or thereof, wherein:
$R_1$ and $R_2$ are taken together to form a structure selected from the group consisting of —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(R)CH=CH—, —CH=CH—N(R)—, —O—CH=CH—, —CH=CH—O—, —S—CH=CH—, —CH=CH—S—, —CH=CH—CH=CH—, —N=CH—CH=CH—, —CH=N—CH=CH—, —CH=CH—N=CH—, —CH=CH—CH=N—, —N=CH—CH=N—, —N=CH—N(R)—, —N(R)—CH=N—, —N(R)—C(=O)N(R$_{15}$)—, —N=CH—O—, —N(R)—C(=O)O—, —O—CH=N—, —O—C(=O)—N(R)—, —N=CH—S—, —N(R)—C(=O)S—, —S—CH=N—, —S—C(=O)—N(R)—, wherein R and $R_{15}$ are independently hydrogen, $C_{1-10}$ alkyl, haloalkyl, aryl, fused aryl, carbocyclic, alkenyl, alkynyl, arylalkyl, arylalkenyl, arylalkynyl, carbocycloalkyl, hydroxyalkyl or aminoalkyl;
$R_3$ and $R_4$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;
$R_5$ is hydrogen or $C_{1-10}$ alkyl; and
$R_{10}$-$R_{14}$ are independently hydrogen halo, haloalkyl, aryl, fused aryl, carbocyclic, $C_{1-10}$ alkyl, alkenyl, alkynyl, arylalkyl, arylalkenvl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkyithiol; or
$R_{10}$ and $R_{11}$, or $R_{11}$ and $R_{12}$, taken together with the atoms to which they are attached to form an aryl or partially saturated carbocyclic group, wherein said group is optionally substituted.

15. A compound of Formula IV:

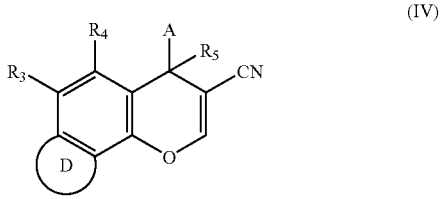

or pharmaceutically acceptable salts or prodrugs thereof, wherein A is optionally substituted and is phenyl or pyridyl; and $R_3$-$R_4$ are independently hydrogen, halo, haloalkyl, aryl, fused aryl, carbocyclic, $C_{1-10}$ alkyl, alkenyl, alkynyl, arylalkyl, arylalkenyl, arylalkynyl, carbocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_3$ and $R_4$, taken together with the atoms to which they are attached to form an aryl or partially saturated carbocyclic group, wherein said group is optionally substituted; $R_5$ is hydrogen or $C_{1-10}$ alkyl; and D is pyrrolo, imidazo, imidazol-2-one, oxazolo, oxazol-2-one, furo, thieno or pyrazo, wherein said group is optionally substituted.

16. The compound of claim 15, wherein $R_3$-$R_4$ are hydrogen.

17. The compound of claim 15, wherein $R_5$ is hydrogen.

18. A compound selected from the group consisting of:
4-(3-Bromo-4,5-dimethoxyphenyl)-3-cyano-7-dimethylamino-4H-chromene;
4-(3-Bromo-4,5-dimethoxyphenyl)-3-cyano-7-ethylamino-4H-chromene;
4-(3-Bromo-4,5-dimethoxyphenyl)-3-cyano-7-methoxy-4H-chromeme;
3-Cyano-4-(5-methyl-3-pyridyl)-4H-indolo[4,5-b]pyran;
4-(5-Bromo-3-pyridyl)-3-cyano-4H-indolo[4,5-b]pyran;
4-(3-Bromo-4,5-dimethoxyphenyl)-3-cyano-4H-indolo[4,5-b]pyran;
4-(3-Bromo-4,5-dimethoxyphenyl)-3-cyano-7-methyl-4H-indolo[4,5-b]pyran;
4-(3-Bromo-4-hydroxy-5-methoxyphenyl)-3-cyano-7-methyl-4H-indolo[4,5-b]pyran;
4-(3-Bromo-4,5-dimethoxyphenyl)-3-cyano-7-ethyl-4H-indolo[4,5-b]pyran;
3-Cyano-7-methyl-4-(5-methyl-3-pyridyl)-4H-indolo[4,5-b]pyran;
4-(5-Bromo-3-pyridyl)-3-cyano-7-methyl-4H-indolo[4,5-b]pyran;
3-Cyano-7-methyl-4-(5-methoxy-3-pyridyl)-4H-indolo[4,5-b]pyran;
4-(3-Bromo-4,5-dimethoxyphenyl)-3-cyano-4H-indolo[7,6-b]pyran;
3-Cyano-7-methyl-4-(3,4,5-trimethoxyphenyl)-4H-indolo[7,6-b]pyran;
4-(3-Bromo-4,5-dimethoxyphenyl)-3-cyano-4H-imidazo[4,5-h]chromene;
4-(3-Bromo-4,5-dimethoxyphenyl)-3-cyano-7-methyl-4H-imidazo[4,5-h]chromene;
4-(3-Bromo-4,5-dimethoxyphenyl)-3-cyano-7-methyl-8-oxo-4H-oxazolo[4,5-h]chromene;
4-(3-Bromo-4,5-dimethoxyphenyl)-3-cyano-4H-furo[2,3-h]chromene;
4-(3-Bromo-4,5-dimethoxyphenyl)-3-cyano-4H-thieno[2,3-h]chromene;
4-(3-Bromo-4,5-dimethoxyphenyl)-3-cyano-4H-pyrazo[2,3-h]chromene;
3-Cyano-7-methoxy-4-(3,4,5-trimethoxyphenyl)-4H-chromene;
3-Cyano-4-phenyl-4H-chromene; and
pharmaceutically acceptable salts or thereof.

19. A composition, comprising the compound of any one of claims 3, 6, 9, 15, and 18, and a pharmaceutically acceptable carrier.

20. The composition of claim 1, wherein B is an optionally substituted benzo.

21. The composition of claim 1, wherein B is an optionally substituted indolo.

22. The composition of claim 1, wherein B is an optionally substituted benzimidazol-2-one.

23. The composition of claim 1, wherein B is an optionally substituted benzoxazol-2-one.

* * * * *